United States Patent [19]

O'Doherty

[11] Patent Number: 5,541,224
[45] Date of Patent: Jul. 30, 1996

[54] CARBANILIDE ANTICOCCIDIALS

[75] Inventor: George O. P. O'Doherty, Greenfield, Ind.

[73] Assignee: Eli Lilly and Company, Indianapolis, Ind.

[21] Appl. No.: 391,751

[22] Filed: Feb. 21, 1995

Related U.S. Application Data

[63] Continuation-in-part of Ser. No. 212,743, Mar. 14, 1994, abandoned, and a continuation-in-part of Ser. No. 384,525, Feb. 13, 1995, abandoned.

[51] Int. Cl.$^6$ .................... A61K 31/255; C07C 309/65
[52] U.S. Cl. .................. 514/517; 558/47; 558/54
[58] Field of Search ................ 558/47, 54; 514/517, 514/460, 451; 549/414, 415, 343

[56] References Cited

U.S. PATENT DOCUMENTS

| B14,218,438 | 12/1983 | Callender et al. |
|---|---|---|
| 2,731,382 | 1/1956 | Basso et al. |
| 3,501,568 | 3/1970 | Haney et al. |
| 3,705,238 | 12/1972 | Hamill et al. |
| 3,719,753 | 3/1973 | Berger et al. |
| 3,857,948 | 12/1974 | Tanaka et al. |
| 4,038,384 | 7/1977 | Berg et al. |
| 4,407,946 | 10/1983 | Labeda et al. |
| 4,468,380 | 8/1984 | O'Doherty et al. |
| 4,582,822 | 4/1986 | Hamill et al. |
| 5,098,834 | 3/1992 | Hamill et al. |

FOREIGN PATENT DOCUMENTS

| 2334355 | 1/1975 | Germany. |
|---|---|---|
| 2653602 | 6/1978 | Germany. |
| 2707488 | 8/1978 | Germany. |
| 1497618 | 4/1975 | United Kingdom. |

OTHER PUBLICATIONS

Kirk–Othmer Encyclopedia of Chemical Technology—4th Ed., vol. #3, pp. 306–322 (1991).
Organic Preparations & Procedures Intl. 9, 175–207 (1977).
Derwent Abstract 05980W/04, Abstracting (English) DE 2 334 355 (1975).

*Primary Examiner*—Nicky Chan
*Attorney, Agent, or Firm*—Kathleen R. S. Page; David E. Boone

[57] ABSTRACT

The present invention is directed to anticoccidial methods, animal feed premixes, and animal feeds, employing a specified carbanilide compound. The present invention is also directed to anticoccidial methods, animal feed premixes, and animal feeds employing the specified carbanilide compound and a polyether antibiotic.

117 Claims, No Drawings

CARBANILIDE ANTICOCCIDIALS

CROSS REFERENCE TO RELATED APPLICATIONS

This is a continuation-in-part of applications Ser. No. 08/212,743, filed Mar. 14, 1994, abandoned, and Ser. No. 08/384,525, filed Feb. 13, 1995, abandoned.

BRIEF DESCRIPTION OF THE INVENTION

Coccidiosis is a disease afflicting animals. It is caused by protozoan organisms, typically the Eimeria. It is particularly devastating among poultry raised in confinement. Many chemotherapeutics are in use to control the disease. However, there is a risk that the causative organisms will develop resistance after continuous or repeated exposure to any particular chemotherapeutic. There is also a desire to employ chemotherapeutics which are active at low rates, in order to minimize the risk of residues, or to reduce the time period during which poultry are untreated prior to slaughter in order to eliminate residues. The search for improved chemotherapeutics for the control of coccidiosis therefore continues.

The present invention provides a new and improved chemotherapeutic for the control of coccidiosis. The invention provides novel carbanilide compounds, methods of employing the compounds for the control of coccidiosis, and animal feed premixes and animal feeds containing the compounds. The invention also include the use of the subject compounds in combination with polyether antibiotics.

DETAILED DESCRIPTION OF THE INVENTION

The novel carbanilide compounds of the present invention are defined by the following formula:

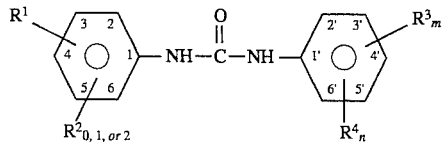

wherein $R^1$ represents perfluoroalkylsulfonyloxy of $C_1$–$C_8$ or 1,1,2,2-tetrafluoroethylsulfonyloxy, with the limitation that if no $R^2$ is present, $R^1$ is located at the 4-position;

$R^3$ represents perfluoroalkylsulfonyloxy of $C_1$–$C_8$ or 1,1,2,2-tetrafluoroethylsulfonyloxy, with the limitation that if no $R^4$ is present, $R^3$ is located at the 4'-position;

each $R^2$ and $R^4$ independently represents nitro, halo, cyano, thiocyanato, trifluoroacetylthio, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;

m represents 0 or 1;

n represents 0, 1, or 2; and the sum of m and n is 1, 2, or 3.

An important element of these compounds is the "$R^1$" group (and the "$R^3$" group when additionally present). The compounds of the present invention wherein both $R^1$ and $R^3$=perfluoroalkylsulfonyloxy are a preferred embodiment of the present invention. Symmetrical compounds are often preferred:

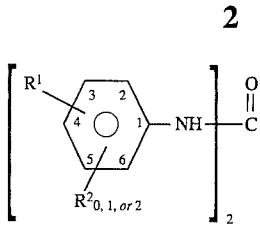

Among the perfluoralkylsulfonyloxy groups, those of $C_1$–$C_5$ are preferred, and those of $C_1$–$C_4$ are often more preferred. The trifluoromethylsulfonyloxy compounds are especially preferred. $R^2$ substituent(s), if present, are preferably located ortho or ortho and para to the $R^1$ substituent. Like preferences pertain to the other ring when it bears an $R^3$ substituent.

Other preferred compounds are of the formula

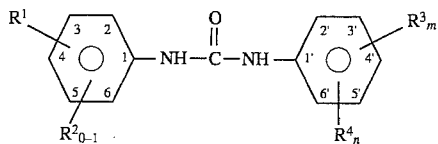

wherein $R^1$ represents perfluoroalkylsulfonyloxy of $C_1$–$C_8$ or 1,1,2,2-tetrafluoroethylsulfonyloxy, located at the 4-position or, when an $R^2$ is located at the 4-position, at the 3-position;

$R^3$ represents perfluoroalkylsulfonyloxy of $C_1$–$C_8$ or 1,1,2,2-tetrafluoroethylsulfonyloxy, located at the 4'-position or, when an $R^4$ is located at the 4'-position, at the 3'-position;

each $R^2$ and $R^4$ independently represents nitro, halo, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;

m represents 0 or 1;

n represents 0, 1, or 2; and the sum of m and n is 1 or 2.

The present carbanilide compounds are prepared by synthesis techniques known for carbanilide compounds. In general, there are two preferred synthetic routes. The first synthetic route is the reaction of an appropriately substituted aniline with an appropriately-substituted isocyanate, to yield the desired compound of the present invention.

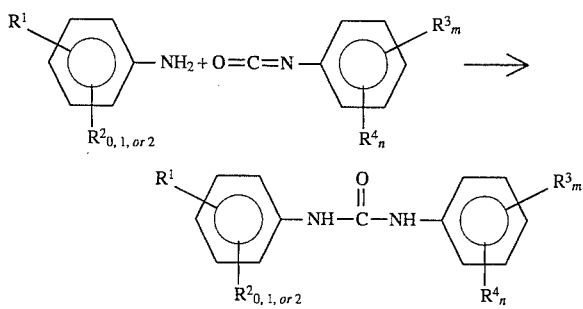

This reaction is conducted in accordance with known conditions for such a reaction. Typically, the reactants are mixed in a reaction medium, which can be a chlorinated hydrocarbon, DMF, THF, ether, or aromatic hydrocarbon. The reaction goes forward under temperatures of a wide variety, such as from 0° C. to 100° C. However, no advantage has been observed in employing lowered or elevated temperatures, and most conveniently, the reaction is simply conducted at room temperature. The reaction consumes the reactants in equimolar amounts, and such are desirably used. The reaction is preferably conducted under nitrogen, in order to prevent oxidation of the aniline. Addition of a small amount of a tertiary amine is catalytic. The product is isolated and purified if desired in standard techniques.

This synthetic route is illustrated by Examples 1–10, below.

A variation of this synthetic route is particularly suited for the preparation of symmetrical compounds of the present invention—that is, compounds wherein m=1, $R^1$=$R^3$, and any additional substitution ($R^2$, $R^4$) is identical. These compounds are conveniently prepared by reacting the aniline as defined above with phosgene, triphosgene, or other reagent which converts the $NH_2$ to an isocyanate. The resulting isocyanate compound reacts directly with remaining aniline to yield the desired symmetrical compound. This variation is illustrated by Examples 11–13, below.

The substituted anilines employed in this synthetic route are themselves prepared from nitrophenols, by reduction of the nitro and esterification of the hydroxy group. The sequence of these two reactions is not critical, except that the $R^1$ group is somewhat unstable under elevated temperatures. Therefore, it is preferred either to reduce first and subsequently esterify; or to esterify first and thereafter reduce the nitro group by dissolving metal reduction, e.g., Zn/Cu/HCl in aqueous methanol at −60° or stannous chloride/HCl/ water. Reduction by $H_2$/Pd is successful only if temperatures can be maintained below about 25° C.

A second preferred synthetic route to the present carbanilide compounds is the esterification of a hydroxycarbanilide by an appropriate reagent, to obtain the desired compound of the present invention:

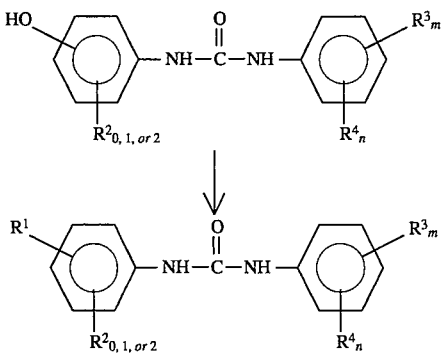

The esterifying agent can be a fluorinated alkylsulfonic acid anhydride of the formula

$$(R^5SO_2)_2O$$

where $R^5$ represents perfluoroalkyl of $C_1$–$C_8$ or 1,1,2,2-tetrafluoroethyl; the corresponding fluoride ($R^5SO_2F$), or an imide of the formula $(R_5SO_2)_2NAr$ where "Ar" is an aryl moiety such as phenyl or pyridyl. The perfluoroalkylsulfonic acid anhydride wherein $R^5$=trifluoromethyl, known as triflic anhydride, is a preferred reagent for the synthesis of the compounds wherein $R^1$ (and $R^3$ if present)=$CF_3SO_2O$—. When the alkyl chain in $R^1$ exceeds two carbons, the fluorides are preferred reagents. The reaction consumes equimolar amounts of the hydroxycarbanilide and esterifying agent, but a slight excess of the esterifying agent is preferred. The reaction generates the corresponding sulfonic acid, and triethylamine or other acid acceptor is typically supplied to the reaction mixture. The reaction proceeds at temperatures over a range, such as from −70° C. to 25° C. Workup and purification are carried out in standard procedures. This synthetic route is illustrated by Examples 14–17 and 19.

In addition to the foregoing synthetic methods, certain of the carbanilides can be prepared from other of the carbanilides, by techniques well known to those skilled in the art. Oxidation of a thio substitutent is one example of this technique; it is illustrated by Example 18.

A review article on "Uses of the Trifyl Group in Organic Synthesis", in *Organic Preparation & Procedures International* 9, 175–207 (1977), is incorporated herein by reference.

The synthesis of the present carbanilide compounds is illustrated by the following examples.

Starting Material: 4-(trifluoromethylsulfonyloxy)aniline p-Nitrophenol (14.00 grams; 0.1 mole) and triethylamine (10.17 grams; 0.1 mole) were mixed in 500 ml of methylene chloride. Triflic anhydride (28.42 grams; 0.1 mole) was added. The reaction mixture was stirred for an hour, checked by TLC, and an additional 2 grams of triflic anhydride added. The reaction mixture was stirred another half hour, then worked up, yielding 4-(trifluoromethylsulfonyloxy)-1-nitrobenzene.

The 4-(trifluoromethylsulfonyloxy)-1-nitrobenzene (27.1 grams; 0.10 mole) in 300 ml of ethanol was added dropwise to 94.8 grams of stannous chloride (0.5 mol; 5 equivalents) in 525 ml of concentrated HCl, at room temperature. The rate of addition was controlled to prevent the temperature of the reaction mixture from rising. The reaction mixture was stirred for 3 hours, 10N NaOH added until the pH was ~12, and extracted into ether. The ether extract was washed with water, dried over magnesium sulfate, and the ether evaporated to yield the desired 4-(trifluoromethylsulfonyloxy)aniline as a yellowish brown oil. Its identity was confirmed by NMR, MS, and elemental analysis, the last of which showed:

|  | Theoretical | Found |
| --- | --- | --- |
| Carbon | 34.85 | 35.10 |
| Hydrogen | 2.51 | 2.57 |
| Nitrogen | 5.81 | 5.89 |

EXAMPLE 1

4'-(Trifluoromethylthio)-4-(Trifluoromethylsulfonyloxy)carbanilide 4-(Trifluoromethylsulfonyloxy)aniline (1.00 gram; 0.0041 mmole) was mixed with 15 ml of methylene chloride, at room temperature and under nitrogen. A few drops of triethylamine were added. 4-(Trifluoromethylthio)phenyl isocyanate (0.90 gram; 0.0041 mole) in 15 ml of methylene chloride was added dropwise, and the resulting reaction mixture was stirred for two hours. An equal volume of cyclohexane was added and the methylene chloride evaporated off, yielding a white solid, which was separated and recrystallized from isopropanol, m.p., 230°–232° C. Elemental analysis showed

|  | Theoretical | Found |
|---|---|---|
| Carbon | 39.13 | 39.39 |
| Hydrogen | 2.19 | 2.26 |
| Nitrogen | 6.09 | 6.19 |

EXAMPLE 2

4'-Nitro-4-(Trifluoromethylsulfonyloxy)carbanilide

The title compound was prepared by reacting 4-nitrophenyl isocyanate with 4-(trifluoromethylsulfonyloxy)aniline in the same general procedures as those in Example 1. The compound melted at 243°–245° C. and had the following elemental analysis:

|  | Theoretical | Found |
|---|---|---|
| Carbon | 41.48 | 41.74 |
| Hydrogen | 2.49 | 2.49 |
| Nitrogen | 10.37 | 10.58 |

EXAMPLE 3

4'-(Trifluoromethyl)-4-(Trifluoromethylsulfonyloxy)carbanilide

The title compound was prepared by reacting 4-(trifluoromethyl)phenyl isocyanate with 4-(trifluoromethylsulfonyloxy)aniline in the same general procedures as those in Example 1. The compound melted at 212°–214° C. and had the following elemental analysis:

|  | Theoretical | Found |
|---|---|---|
| Carbon | 42.06 | 41.94 |
| Hydrogen | 2.35 | 2.38 |
| Nitrogen | 6.54 | 6.31 |

EXAMPLES 4 & 5

4'-Chloro-3'-(Trifluoromethyl)-4-(Trifluoromethylsulfonyloxy)carbanilide and 2'-Chloro-3'-(Trifluoromethyl)-4-(Trifluoromethylsulfonyloxy)carbanilide The title compounds were prepared by reacting 4-chloro-3-(trifluoromethyl)phenyl isocyanate with 4-(trifluoromethylsulfonyloxy)aniline in the same general procedures as those in Example 1. The 4'-chloro-3'-(trifluoromethyl)isomer melted at 192°–194° C. and had the following elemental analysis:

|  | Theoretical | Found |
|---|---|---|
| Carbon | 38.93 | 39.67 |
| Hydrogen | 1.96 | 2.05 |
| Nitrogen | 6.05 | 6.01 |

The 2'-chloro-3'-(trifluoromethyl)isomer melted at 167°–170° C. and had the following elemental analysis:

|  | Theoretical | Found |
|---|---|---|
| Carbon | 38.93 | 40.12 |
| Hydrogen | 1.96 | 2.21 |
| Nitrogen | 6.05 | 5.89 |

It contained a small amount of starting material.

EXAMPLE 6

4'-Bromo-4-(Trifluoromethylsulfonyloxy)carbanilide

The title compound was prepared by reacting 4-bromophenyl isocyanate with 4-(trifluoromethylsulfonyloxy)aniline in the same general procedures as those in Example 1. The compound melted at 207°–208° C. and had the following elemental analysis:

|  | Theoretical | Found |
|---|---|---|
| Carbon | 38.28 | 38.15 |
| Hydrogen | 2.29 | 2.39 |
| Nitrogen | 6.38 | 6.42 |

EXAMPLE 7

4'-Chloro-2'-(Trifluoromethyl)-4-(Trifluoromethylsulfonyloxy)carbanilide

The title compound was prepared by reacting 4-chloro-2-(trifluoromethyl)phenyl isocyanate with 4-(trifluoromethylsulfonyloxy)aniline in the same general procedures as those in Example 1. The compound melted at 160°–161° C. and had the following elemental analysis:

|  | Theoretical | Found |
|---|---|---|
| Carbon | 38.92 | 38.95 |
| Hydrogen | 1.96 | 2.14 |
| Nitrogen | 6.05 | 6.29 |

EXAMPLE 8

2'-Chloro-5'(Trifluoromethyl)-4-(Trifluoromethylsulfonyloxy)carbanilide

The title compound was prepared by reacting 2-chloro-5-(trifluoromethyl)phenyl isocyanate with 4-(trifluoromethylsulfonyloxy)aniline in the same general procedures as those in Example 1. The compound melted at 184°–187° C. and had the following elemental analysis:

|  | Theoretical | Found |
|---|---|---|
| Carbon | 38.92 | 39.21 |
| Hydrogen | 1.96 | 2.03 |
| Nitrogen | 6.05 | 6.11 |

EXAMPLE 9

4'-(Trifluoromethylthio)-3-Chloro-4-(Trifluoromethylsulfonyloxy)carbanilide

The title compound was prepared by reacting 4-trifluoromethyl)phenyl isocyanate with 3-chloro-4-(trifluoromethylsulfonyloxy)aniline in the same general procedures as those in Example 1. The compound melted at 207°–209° C. and had the following elemental analysis:

|  | Theoretical | Found |
|---|---|---|
| Carbon | 36.41 | 36.70 |
| Hydrogen | 1.83 | 2.10 |
| Nitrogen | 5.66 | 5.43 |

EXAMPLE 10

4'-(1,1,2,2-Tetrafluoroethylthio)-4-(Trifluoromethylsulfonyloxy)carbanilide

The title compound was prepared by reacting 4-(1,1,2,2-tetrafluoroethylthio)phenyl isocyanate with 4-(trifluoromethylsulfonyloxy)aniline in the same general procedures as those in Example 1. The compound melted at 213°–215° C. The compound can be oxidized per Example 18, to obtain the corresponding 4'-(1,1,2,2-tetrafluoroethylsulfonyl) compound.

EXAMPLE 11

4,4'-Bis(Trifluoromethylsulfonyl)carbanilide 4-(Trifluoromethylsulfonyloxy)aniline (2.1 gram; 0.001 mole) and triphosgene (0.6 gram; 0.003 mole) were mixed in 60 ml. of 1.2 dichloroethane. The reaction mixture was stirred and heated to reflux while triethylamine (3 ml.) was added dropwise. After refluxing for one hour, the reaction mixture was a clear solution. It was equilibrated with 100 ml. of ether and with 50 ml. of 2N HCl. The solution was then dried over magnesium sulfate and evaporated to dryness. The residue was slurried with 10 ml. of 1,2-dichlorethane and 50 ml. of cyclohexane, and filtered to isolate the product as a white solid. It melted at 238°–240° C. and had the following elemental analysis:

|  | Theoretical | Found |
|---|---|---|
| Carbon | 35.44 | 35.21 |
| Hydrogen | 1.98 | 2.18 |
| Nitrogen | 5.51 | 5.27 |

EXAMPLE 12

3,3'-Dichloro-4,4'-Bis(Trifluoromethylsulfonyloxy)carbanilide

The title compound was prepared by reacting 3-chloro-4-(trifluoromethylsulfonyloxy)aniline with triphosgene in the same general procedures as those of Example 11. The product melted at 252°–253° C.

EXAMPLE 13

3,3'-Bis(Trifluoromethyl)-4,4'-Bis(TriFluoromethylsulfonyloxy)carbanilide

The title compound was prepared by reacting 3-(trifluoromethyl)-4-(trifluoromethylsulfonyloxy)aniline with triphosgene in the same general procedures as those of Example 11. The product melted at 218°–220° C.

EXAMPLE 14

4'-Chloro-3,3'-Bis(Trifluoromethyl)-4-(Trifluoromethylsulfonyloxy)carbanilide 4'-Chloro-3,3'-bis(trifluoromethyl)-4-hydroxycarbanilide (1.00 gram; 2.51 mole) was added to 10 ml. of methylene chloride. Triflic anhydride (9.78 gram; 2.76 mole) was added, dropwise, followed by triethylamine (0.56 gram; 5.52 mmole), also added dropwise. The reaction mixture turned a deep purple in color. After three hours, the reaction mixture was evaporated to a dark purple gum. NMR showed the desired product as well as triethylamine. The gum was chromatographed over a two-inch pad of silica in methylene chloride, taking 50-ml. cuts. Cuts 1–6 contained the product and cuts 3–5 were combined and evaporated to a light brown foam. Ether was added to the foam and evaporated to an off-white foam. The identity of the product was confirmed by NMR.

EXAMPLE 15

3',4'-Dichloro-3-(Trifluoromethyl)-4-(Trifluoromethylsulfonyloxy)carbanilide 3',4'-Dichloro-3-(trifluoromethyl)-4-hydroxycarbanilide and triflic anhydride were reacted, in essentially the same procedures as Example 14, to yield the title compound, m.p. 170°–172° C.

EXAMPLE 16

4'-Nitro-3-(Trifluoromethyl)-4-hydroxycarbanilide (Trifluoromethylsulfonyloxy)carbanilide 4'-Nitro-3-(trifluoromethyl)-4-hydroxycarbanilide and triflic anhydride were reacted, in essentially the same procedures as Example 14, to yield the title compound. It melted at 226°–227° C. and had the following elemental analysis:

|  | Theoretical | Found |
|---|---|---|
| Carbon | 38.07 | 38.49 |
| Hydrogen | 1.92 | 2.13 |
| Nitrogen | 8.88 | 9.04 |

EXAMPLE 17

3,4'-Bis(Trifluoromethyl)-4-(Trifluoromethylsulfonyloxy)carbanilide 3,4'-Bis(trifluoromethyl)-4-hydroxycarbanilide and triflic anhydride were reacted in essentially the same procedures as Example 14, to yield the title compound. It melted at 141°–143° C. with decomposition and had the following elemental analysis:

|  | Theoretical | Found |
|---|---|---|
| Carbon | 38.72 | 38.98 |
| Hydrogen | 1.83 | 2.01 |
| Nitrogen | 5.64 | 5.83 |

EXAMPLE 18

4'-(Trifluoromethylsulfinyl)-4-(Trifluoromethylsulfonyloxy)carbanilide and 4'-(Trifluoromethylsulfonyl)-4-(Trifluoromethylsulfonyloxy)carbanilide

4'-(Trifluoromethylthio)-4-(trifluoromethylsulfonyloxy)carbanilide (6 grams; 0.012 mole) and 33 percent hydrogen peroxide (9 ml) were mixed and stirred at 25° C. in 40 ml of trifluoroacetic acid. A precipitate formed after about 10 minutes; TLC suggested the sulfinyl (S=O) compound. The reaction mixture was stirred at 25° C. for 16 hours, when TLC showed both sulfinyl and sulfonyl groups. The reaction mixture was then heated to 60° C. for one hour, and subsequently cooled and stirred at 25° C. for 24 hours. Water (60 ml) was added and the reaction mixture filtered; the isolated sulfonyl product was air dried and recrystalized from 1,2-dichloroethane, m.p., 256°–257° C. (dec.). The product had the following elemental analysis:

|  | Theoretical | Found |
|---|---|---|
| Carbon | 36.59 | 36.64 |
| Hydrogen | 2.05 | 2.00 |
| Nitrogen | 5.69 | 5.67 |

EXAMPLE 19

4'-(Trifluoromethylthio)-4-(Trifluoromethylsulfonyloxy)carbanilide

This compound, illustrated in Example 1, was also prepared by an alternate method. In this alternate preparation, 4'-(trifluoromethylthio)-4-hydroxycarbanilide (2.60 grams; 0.008 mmole) was mixed with 20 ml. of methylene chloride at 0° C. Triethylamine (0.88 gram; 0.0088 mole) was added, dropwise, followed by triflic anhydride (2.46 grams; 0.0088 mmole) in a small amount of methylene chloride. The reaction mixture was stirred at 0° C. for four hours, during which time samples were withdrawn at various times and checked by thin layer chromatography for the presence of starting material. After the first two samplings, additional triflic anhydride and triethylamine were added. The third sample indicated virtually no starting material and the reaction mixture was worked up.

The methylene chloride was evaporated off, about 75 ml. of ether was added, and the resulting mixture was washed three times with 1N HCl, dried over magnesium sulfate, and evaporated to remove the ether. The residue was slurried in methylene chloride, filtered, washed with 2N NaOH, and filtered. The product had the following elemental analysis:

|  | Theoretical | Found |
|---|---|---|
| Carbon | 39.13 | 39.39 |
| Hydrogen | 2.19 | 2.26 |
| Nitrogen | 6.09 | 6.13 |

EXAMPLE 20

4'-(Trifluoromethylsulfonyl)-3-nitro-4-(trifluoromethylsulfonyl(carbanilide

4'-(Trifluoromethylsulfonyl)-3-nitro-4-hydroxycarbanilide and triflic anhydride were reacted in essentially the same procedures as Example 14, to yield the title compound. It melted at 175°–176° C. and had the following elemental analysis:

|  | Theoretical | Found |
|---|---|---|
| Carbon | 33.52 | 33.82 |
| Hydrogen | 1.69 | 1.81 |
| Nitrogen | 7.82 | 7.56 |

Other representative compounds of the present invention include the following:

4'-(trifluoromethylthio)-4-(1,1,2,2-tetrafluoroethylsulfonyloxy)carbanilide

4'-(trifluoromethylsulfonyl)-4-(1,1,2,2-tetrafluoroethylsulfonyloxy)carbanilide

4'-(1,1,2,2-tetrafluoroethylthio)-4-(1,1,2,2-tetrafluoroethylsulfonyloxy)carbanilide 4'-(trifluoromethylthio)-4-(perfluoro-n-butylsulfonyloxy)carbanilide 4'(1,1,2,2-tetrafluoroethylthio)-4-(perfluoro-n-butylsulfonyloxy)carbanilide 4'-(1,1,2,2-tetrafluoroethylsulfonyl)-4-(perfluoro-n-butylsulfonyloxy)carbanilide 4'-(trifluoromethylthio)-4-(perfluoro-n-octylsulfonyloxy)carbanilide 4'-(trifluoromethylsulfonyl)-4-(perfluoro-n-octylsulfonyloxy)carbanilide 4'-(1,1,2,2-tetrafluoroethylthio)-4-(perfluoro-n-octylsulfonyloxy)carbanilide 4'-(1,1,2,2-tetrafluoroethylsulfonyl)-4-(perfluoro-n-octylsulfonyloxy)carbanilide 4'-(trifluoromethylsulfonyl)-3-nitro-5-(trifluoromethyl)-2-(trifluoromethylsulfonyloxy)carbanilide 4'-(trifluoromethylsulfonyl)-3-nitro-5-(trifluoromethyl)-2-(perfluoro-n-butylsulfonyloxy)carbanilide 4'-(trifluoromethylsulfonyl)-3-(trifluoromethyl)-4-(trifluoromethylsulfonyloxy)carbanilide 4'-(trifluoromethylsulfonyl)-3-chloro-5-(trifluoromethyl)-4-(trifluoromethylsulfonyloxy)carbanilide 4'-(trifluoromethylsulfonyl)-3-nitro-5-(trifluoromethyl)-4-(trifluoromethylsulfonyloxy)carbanilide 4'-(trifluoromethylsulfonyl)-3-(trifluoromethyl)-4-(perfluoro-n-butylsulfonyloxy)carbanilide 4'-(trifluoromethylsulfonyl)-3-chloro-5-(trifluoromethyl)-4-(perfluoro-n-butylsulfonyloxy)carbanilide 4'-(trifluoromethylsulfonyl)-3-nitro-5-(trifluormethyl)-4-(perfluoro-n-butylsulfonyloxy)carbanilide 4'-thiocyanato-3-chloro-5-(trifluoromethyl)-4-(trifluoromethylsulfonyloxy)carbanilide 4'-thiocyanato-3-(trifluoromethyl)-4-(trifluoromethylsulfonyloxy)carbanilide 4'-(trifluoromethylsulfonyl)-3-chloro-4-(trifluoromethylsulfonyloxy)carbanilide 4'-(trifluoromethylsulfonyl)-3,5-dichloro-4-(trifluoromethylsulfonyloxy)carbanilide 4'-(trifluoromethylsulfonyl)-3-fluoro-4-(trifluoromethylsulfonyloxy)carbanilide 4'-(trifluoromethylsulfonyl)-3,5-difluoro-4-(trifluoromethylsulfonyloxy)carbanilide 4'-(trifluoromethylsulfonyl) -3-chloro-4-(perfluoro-n-butylsulfonyloxy)carbanilide 4'-(trifluoromethylsulfonyl)-3,5-dichloro-4-(perfluoro-n-butylsulfonyloxy)carbanilide 4'-(trifluoromethylsulfonyl)-3-fluoro-4-(perfluoro-n-butylsulfonyloxy)carbanilide 4'-(trifluoromethylsulfonyl)-3,5-difluoro-4-(perfluoro-n-butylsulfonyloxy)carbanilide 3,3'-bis(trifluoromethyl)-4,4'-bis(trifluoromethylsulfonyloxy)carbanilide 3,3'-bis(trifluoromethyl)-4,4'-bis(perfluoro-n-butylsulfonyloxy)carbanilide 3,3'-difluoro-4,4'-bis(trifluoromethylsulfonyloxy)carbanilide 3,3'-difluoro-4,4'-bis(perfluoro-n-butylsulfonyloxy)carbanilide 3,3'-dichloro-4,4'-bis(trifluoromethylsulfonyloxy)carbanilide 3,3'-dichloro-4,4'-bis(perfluoro-n-butylsulfonyloxy)carbanilide 3,3',5,5'-tetrachloro-4,4'-bis(trifluoromethylsulfonyloxy)carbanilide 4'-(trifluoromethylsulfonyl)-3-cyano-4-(trifluoromethylsulfonyloxy)carbanilide 4'-(trifluoromethylsulfonyl)-3-cyano-4-(perfluoro-n-butylsul fonyloxy)carbanilide 4'-(trifluoromethylsulfonyl)-3-chloro-5-cyano-4-(trifluoromethylsulfonyloxy)carbanilide 4'-(trifluoromethylsulfonyl)-3-chloro-5-cyano-4-(perfluoro-n-butylsulfonyloxy)carbanilide 4'-thiocyanato-3-cyano-4-(perfluoro-n-butylsulfonyloxy) carbanilide 4'-thiocyanato-3-chloro-5-cyano-4-(perfluoro-n-butylsulfonyloxy)carbanilide 4'-(trifluoroacetylthio)-4-(trifluoromethylsulfonyloxy) carbanilide 4'-(trifluoroacetylthio)-3-chloro-4-(trifluoromethylsulfonyloxy)carbanilide 4'-(trifluoroacetylthio)-3,5-dichloro-4-(trifluoromethylsulfonyloxy)carbanilide 4'-(trifluoroacetylthio)-3-fluoro-4-(trifluoromethylsulfonyloxy)carbanilide 4'-nitro-4-(perfluoro-n-pentylsulfonyloxy)carbanilide The present invention can be employed for the control of coccidiosis in any species. Chickens and turkeys are the species most commonly treated for coccidiosis but the present invention can also be used with other poultry species, such as ducks, geese, quail, pheasants and ostriches. The invention can also be practiced with species other than poultry, such as cattle, sheep, swine, and the like.

The present invention can be used to prevent or treat coccidiosis attributable to any species. The species which commonly cause coccidiosis in chickens are

*Eimeria acervulina*

*Eimeria brunetti*

*Eimeria maxima*

*Eimeria necatrix*

*Eimeria tenella*

The species which commonly cause coccidiosis in turkeys are

*Eimeria meleagrimitis*

*Eimeria gallopavonis*

*Eimeria adenoeides*

*Eimeria dispersa*

Coccidiosis in other species is attributable to yet other protozoan species known to those skilled in the art.

The present invention is practiced in the usual fashion of anticoccidials, that is, because coccidiosis is a malady of the intestinal tract, an anticoccidial must be administered in a way to reach the intestinal tract. This is typically achieved by incorporating the present agents in the feed. Anticoccidials are sometimes administered via the drinking water, and this route is also possible for the present carbanilide compounds. In the most preferred practice, however, the present compounds are administered in the feed.

The present invention contemplates using a carbanilide compound as sole anticoccidial agent; it also contemplates using the carbanilide in combination with a polyether antibiotic.

The polyethers are a known class of antibiotics sharing common structural features. A review article is found in the Kirk-Othmer Encyclopedia of Chemical Technology—4th Ed., Volume # 3, pages 306–322, and this article is incorporated herein by reference. The polyethers exhibit anticoccidial activity, and are presently the principal chemotherapeutics, worldwide, for the control of coccidiosis.

Field use of most anticoccidials other than the polyethers lead to the rapid development or selection of resistant strains. This meant that such anticoccidials were of very little subsequent value. The polyethers are unique in respect to the matter of resistance. Some resistance has been confirmed. It is not widespread in occurrence, and when it does occur, it generally does not lead to a complete loss of efficacy. Because of this and their other advantages, the polyether antibiotics remain an efficacious tool for the control of coccidiosis.

The present carbanilides are able to control coccidiosis attributable to polyether-resistant strains. Combinations of the present carbanilides and the polyethers likewise control coccidiosis attributable to polyether-resistant strains. Further, the use of such combinations is expected to prevent or delay the development of polyether resistance, and thus provides a new tool in the prevention and treatment of coccidiosis. Therefore, in one embodiment of the present invention, a carbanilide is used as sole anticoccidial, or in combination with a polyether, to prevent or treat coccidiosis due to a polyether-resistant protozoan.

Representative polyethers which can be used in the present invention include the following; the noted reference patents are incorporated herein by reference.

| | |
|---|---|
| monensin | 3,501,568 |
| laidlomycin | |
| nigericin | |

13
-continued

| | |
|---|---|
| grisorixin | |
| dianemycin | |
| lenoremycin | |
| salinomycin | 3,857,948 |
| narasin | 4,038,384 |
| lonomycin | |
| antibiotic X206 | |
| allorixin | |
| septamycin | |
| antibiotic A204 | 3,705,238 |
| etheromycin | |
| lasalocid | 3,719,753 |
| isolasalocid | |
| lysocellin | |
| antibiotic A23187 | 4,582,822 |
| portmicin (antibiotic A80190) | 4,683,204 |
| kijimicin | |
| antibiotic A82810 | 5,098,834 |
| maduramicin factor A (X-4868A) | 4,407,946 |
| maduramicin factor C (LLC-23024B) | |
| semduramicin. | |

The present active agents are incorporated into an animal feed in the manner usual for anticoccidials. Typically, a carbanilide compound, or a carbanilide compound as well as a polyether, are incorporated into a "premix." The premix contains the active agent or agents as well as physiologically acceptable carriers and feedstuffs. The premix is relatively concentrated and is adapted to be diluted with other carriers, vitamin and mineral supplements, and feedstuffs to form the final animal feed. Premixes which are intermediate in concentration of active agent between a first premix and the final animal feed are sometimes employed in the industry and can be used in implementing the present invention.

When employing a carbanilide compound as sole active agent, a premix desirably contains the agent at a concentration of from 0.1 to 50.0% by weight. Preferred premixes will generally contain a carbanilide compound at a concentration of from 0.5 to 25.0%, by weight. When employing both a carbanilide compound as well as a polyether, a premix desirably contains concentrations of from 0.2 to 25.0% by weight of each active agent. Combined therapy can also be obtained using one premix containing the carbanilide compound and a second premix containing the polyether. Both mixes are added to carriers, vitamin and mineral supplements, and feedstuffs to yield a single animal feed containing both active agents. The identity of the other components of the premix and ultimate animal feed is not critical; exemplary formulations are listed below.

In final feeds, the concentration of the carbanilide, and polyether if employed, is not critical and will depend on various factors known to those skilled in the art. Such factors include the relative potency of the particular carbanilide and polyether; and the severity of the coccidial challenge. In general, a final feed employing a carbanilide as sole active agent will contain the carbanilide in a concentration of from 0.001 to 0.02% by weight. In the case of combined therapy, a final feed will typically contain the carbanilide at a concentration of from 0.0001% to 0.01% by weight, and the polyether at a concentration of from 0.0001% to 0.01% by weight.

The advantages of combined therapy are maximized if each of the two active agents makes a significant contribution to the overall anticoccidial action. In general, the carbanilide and polyether are employed in a ratio of from 1:5 to 5:1. Those skilled in the art will readily be able to determine suitable concentrations of carbanilide and polyether antibiotic.

Various compounds to be employed in accordance with the present invention were evaluated in a standardized battery test. In this test, the respective compound was mixed well with a small portion of a basal diet, to constitute a premix, and the resulting premix was added to a large amount of the same basal diet. This resulted in the ultimate diet fed to the birds, containing the respective compound. This diet was in the form of a mash.

The battery test was conducted with Peterson x Hubbard cockerel chicks or Nicholas hen turkey poults, beginning when the birds were approximately nine days old. There were generally four birds per pen and one to four pens per treatment. All birds were housed in stainless steel wire cages, 13"×21"×9". The respective diet and water were provided ad libitum beginning at approximately day nine. All birds except those of a non-infected control group were infected with two or three species of Eimeria. Some of the strains exhibited resistance to the polyethers. Infection was by crop intubation of sporulated oocysts, usually two days after the trial began (in some tests, one day after the trial began). The birds were maintained on the trial for approximately nine days at which time they were killed and the intestinal tracts evaluated for the degree of lesions attributable to coccidiosis. Other parameters evaluated during the test were mortality, weight gain, and feed/gain.

The composition of the basal feed for chicks was as follows:

| Ingredients | % |
|---|---|
| Ground yellow corn | 51.796 |
| Soybean meal (48.5%) | 34.626 |
| Animal tallow | 6.970 |
| meat and bone meal | 4.000 |
| Salt (NaCl) | 0.355 |
| Dicalcium phosphate | 0.601 |
| D,L-methionine | 0.276 |
| Ground limestone | 0.926 |
| Trace mineral premix, CK-01 (1.00)[1] | 0.100 |
| Vitamin premix, CK-02 (1.03)[2] | 0.250 |
| Selenium premix, .02%[3] | 0.100 |
| Total | 100.00 |

[1]Trace mineral premixes provides 80 mg of Mn, 75 mg of Zn, 60 mg of Fe, 8 mg of Cu, and 1 mg of I per kg of complete feed.
[2]Vitamin premix provides 8000 IU of vitamin A, 2700 ICU of vitamin $D_3$, 20 mg of vitamin E, 1.5 mg of vitamin K, 45 mg of niacin, 12 mg of pantothenic acid, 8 mg of riboflavin, 3 mg of pyridoxine, 2 mg of thiamine, 800 µg of folic acid, 80 µg of biotin, 15 µg of vitamin $B_{12}$, 500 mg of choline and 125 mg of ethoxyquin per kg of complete feed.
[3]Selenium premix provides 200 µg Se per kg of complete feed.

The composition of the feed for turkey poults was as follows:

| Ingredients | % |
|---|---|
| Corn, Yellow, Ground | 31.9 |
| Soybean Oil Meal, Solvent Extracted Dehulled (49%) | 46.0 |
| Animal Fat (Beef Tallow) | 5.0 |
| Fish Meal with Solubles | 5.0 |
| Alfalfa meal, Dehydrated (17%) | 2.5 |
| Corn Distillers Dried Solubles | 5.0 |
| Dicalcium Phosphate, Feed Grade | 2.2 |
| Calcium Carbonate (Ground Limestone) | 1.4 |
| Vitamin Premix TK-01 (1.03)[1] | 0.5 |
| Salt (NaCl) | 0.3 |
| Trace Mineral Premix TK-01 (1.02)2 | 0.1 |
| Methionine Hydroxy Analog | 0.1 |
| Total | 100.0 |

[1]Vitamin premix provides 3000 IU of vitamin A, 900 ICU of vitamin D, 40 mg of vitamin E, 0.7 mg of vitamin K, 1000 mg of choline, 0.10 mg of vitamin B12, 0.10 mg of biotin and 125 mg of ethoxyquin per kg of complete feed.
[2]Trace mineral premix provides 75 mg of Mn, 50 mg of Zn, 25 mg of Fe and 1 mg of I per kg of complete feed.

The final feeds contained the respective carbanilide compound in concentrations of from 10 to 100 ppm, which is equivalent to 0.001 to 0.01% by weight. In those trials of combined therapy, the carbanilide compound was present in concentrations of 10 to 60 ppm, equivalent to 0.001 to 0,006% by weight, and the polyether was present in concentrations of 10 to 60 ppm, equivalent to 0.001 to 0.006% by weight.

Results of the trials conducted as described above are reported in the following tables. "#" columns refer to the number of pens. Mortality is reported using both (1) due to all causes ("Total"), and (2) due to coccidiosis ("DTC"), only. Weight gain is calculated only for surviving chicks. The calculation of feed:gain ratio includes mortality weights. Lesions were scored on a scale of 0–12 (intestinal) and 0–4 (cecal), with 0 indicating no lesions and 12 or 4 indicating maximum lesions. Statistical analyses were by the Student-Newman-Keul's Multiple Range Test, using Gerbhardt's Algorithm for unequal sample size. Means within a column with no common superscript letter differ (P<0.05).

TABLE 1

Inoculated with *E. acervulina* and *E. tenella*

| Treatment | Mortality | | | | Mean Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 2 | 0.0 a | 2 | 0.0 a | 2 | 255.4 a | 2 | 1.343 a | 2 | 0.00 c | 2 | 0.00 b |
| IC 0 | 2 | 0.0 a | 2 | 0.0 a | 2 | 177.5 b | 2 | 1.657 a | 2 | 6.00 a | 2 | 3.63 a |
| Example 1 | | | | | | | | | | | | |
| 20 | 2 | 12.5 a | 2 | 0.0 a | 2 | 192.4 a–b | 2 | 1.981 a | 2 | 6.63 a | 2 | 3.67 a |
| 40 | 2 | 0.0 a | 2 | 0.0 a | 2 | 196.7 a–b | 2 | 1.692 a | 2 | 2.75 b | 2 | 1.13 b |
| 60 | 2 | 12.5 a | 2 | 0.0 a | 2 | 238.9 a–b | 2 | 1.482 a | 2 | 0.67 c | 2 | 0.46 b |
| 80 | 2 | 0.0 a | 2 | 0.0 a | 2 | 225.0 a–b | 2 | 1.440 a | 2 | 0.00 c | 2 | 0.38 b |
| Source of Variance | df | Mean Square | df | Mean Square | df | Mean Square | df | Mean Square | df | Mean Square | df | Mean Square |
| Treat. | 5 | 83.3 | 5 | 0.0 | 5 | 1820.7 | 5 | 0.105 | 5 | 18.00 | 5 | 5.58 |
| Error | 6 | 104.2 | 6 | 0.0 | 6 | 332.5 | 6 | 0.061 | 6 | 0.33 | 6 | 0.15 |

TABLE 2

Inoculated with *E. tenella* and *E. acervulina*

| Treatment | Mortality | | | | Mean Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 a | 4 | 0.0 a | 4 | 358.5 a | 4 | 1.335 c | 4 | 0.25 c | 4 | 0.13 b |
| IC 0 | 4 | 6.3 a | 4 | 6.3 a | 4 | 216.0 c | 4 | 1.853 a | 4 | 8.75 a | 4 | 3.88 a |
| Example 1 | | | | | | | | | | | | |
| 40 | 4 | 0.0 a | 4 | 0.0 a | 4 | 343.6 a | 4 | 1.366 c | 4 | 0.19 c | 4 | 0.31 b |
| 50 | 4 | 0.0 a | 4 | 0.0 a | 4 | 330.2 a–b | 4 | 1.360 c | 4 | 0.06 c | 4 | 0.38 b |
| 60 | 4 | 0.0 a | 4 | 0.0 a | 4 | 312.2 a–b | 4 | 1.381 c | 4 | 0.00 c | 4 | 0.06 b |
| 70 | 4 | 0.0 a | 4 | 0.0 a | 4 | 294.5 b | 4 | 1.478 b–c | 4 | 0.00 c | 4 | 0.00 b |
| 80 | 4 | 0.0 a | 4 | 0.0 a | 4 | 228.7 c | 4 | 1.722 a–b | 4 | 0.00 c | 4 | 0.06 b |
| Source of Variance | df | Mean Square | df | Mean Square | df | Mean Square | df | Mean Square | df | Mean Square | df | Mean Square |
| Treat. | 7 | 174.1 | 7 | 55.1 | 7 | 11623.4 | 7 | 0.217 | 7 | 39.52 | 7 | 9.77 |
| Error | 22 | 78.1 | 22 | 35.5 | 22 | 534.1 | 22 | 0.028 | 22 | 0.28 | 22 | 0.04 |

TABLE 3

Inoculated with *E. tenella*, laboratory strain, and *E. maxima*

| Treatment | Mortality | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 b | 4 | 0.0 b | 4 | 368.3 a | 4 | 1.325 c | 4 | 0.19 c | 4 | 0.00 c |
| IC 0 | 4 | 25.0 a–b | 4 | 25.0 a | 4 | 147.9 d | 4 | 2.490 a | 4 | 8.06 a | 4 | 3.94 a |
| Example 1 | | | | | | | | | | | | |
| 40 | 4 | 6.3 b | 4 | 0.0 b | 4 | 303.6 b | 4 | 1.542 c | 4 | 4.08 b | 4 | 1.06 b |
| 50 | 4 | 0.0 b | 4 | 0.0 b | 4 | 322.0 b | 4 | 1.410 c | 4 | 1.00 c | 4 | 0.56 b–c |
| 60 | 4 | 6.3 b | 4 | 0.0 b | 4 | 327.1 b | 4 | 1.438 c | 4 | 0.31 c | 4 | 0.15 c |
| 70 | 4 | 0.0 b | 4 | 0.0 b | 4 | 317.1 b | 4 | 1.395 c | 4 | 0.13 c | 4 | 0.00 c |
| 80 | 4 | 6.3 b | 4 | 0.0 b | 4 | 225.0 c | 4 | 1.826 b | 4 | 0.25 c | 4 | 0.00 c |
| Source of Variance | df | Mean Square | df | Mean Square | df | Mean Square | df | Mean Square | df | Mean Square | df | Mean Square |
| Treat. | 7 | 528.3 | 7 | 428.6 | 7 | 20411.8 | 7 | 0.632 | 7 | 35.58 | 7 | 8.96 |
| Error | 22 | 134.9 | 22 | 56.8 | 22 | 639.9 | 22 | 0.026 | 22 | 1.83 | 22 | 0.12 |

TABLE 4

Inoculated with *E. meleagrimitis*, *E. gallopavonis*, and *E. adenoeides*

| Treatment | Mortality | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 2 | 0.0 a | 2 | 0.0 a | 2 | 177.9 a | 2 | 1.240 b | 2 | 0.00 d | 2 | 0.00 b |
| IC 0 | 2 | 0.0 a | 2 | 0.0 a | 2 | 97.3 b | 2 | 1.766 a | 2 | 7.75 a | 2 | 2.63 a |
| Example 1 | | | | | | | | | | | | |
| 20 | 2 | 0.0 a | 2 | 0.0 a | 2 | 112.2 b | 2 | 1.628 a | 2 | 6.63 a–b | 2 | 0.38 b |
| 40 | 2 | 0.0 a | 2 | 0.0 a | 2 | 149.1 a | 2 | 1.374 b | 2 | 6.63 a–b | 2 | 0.00 b |
| 60 | 2 | 0.0 a | 2 | 0.0 a | 2 | 174.6 a | 2 | 1.283 b | 2 | 6.38 a–b | 2 | 0.00 b |
| 80 | 2 | 0.0 a | 2 | 0.0 a | 2 | 164.6 a | 2 | 1.214 b | 2 | 4.25 a–c | 2 | 0.00 b |
| 20 | 2 | 0.0 a | 2 | 0.0 a | 2 | 172.4 a | 2 | 1.277 b | 2 | 0.63 c–d | 2 | 0.00 b |
| 40 | 2 | 0.0 a | 2 | 0.0 a | 2 | 180.5 a | 2 | 1.300 b | 2 | 1.25 c–d | 2 | 0.00 b |
| 60 | 2 | 0.0 a | 2 | 0.0 a | 2 | 185.6 a | 2 | 1.218 b | 2 | 3.63 b–d | 2 | 0.00 b |
| 80 | 2 | 0.0 a | 2 | 0.0 a | 2 | 174.6 a | 2 | 1.197 b | 2 | 0.63 c–d | 2 | 0.00 b |
| Source of Variance | df | Mean Square | df | Mean Square | df | Mean Square | df | Mean Square | df | Mean Square | df | Mean Square |
| Treat. | 9 | 0.0 | 9 | 0.0 | 9 | 1847.8 | 9 | 0.074 | 9 | 17.67 | 9 | 1.36 |
| Error | 10 | 0.0 | 10 | 0.0 | 10 | 157.4 | 10 | 0.005 | 10 | 1.23 | 10 | 0.03 |

TABLE 5

Inoculated with *E. acervulina*, *E. maxima*, and *E. tenella*

| Treatment | Mortality | | | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 2 | 0.0 a | 2 | 0.0 a | 2 | 336.6 a–b | 2 | 1.323 c | 2 | 0.00 f | 2 | 0.00 b |
| IC 0 | 2 | 0.0 a | 2 | 0.0 a | 2 | 286.2 b–c | 2 | 1.552 a | 2 | 6.88 a–b | 2 | 3.75 a |

TABLE 5-continued

Inoculated with *E. acervulina*, *E. maxima*, and *E. tenella*

Example 1

| | | | | | | | | | | | |
|---|---|---|---|---|---|---|---|---|---|---|---|
| 10 | 2 | 0.0 a | 2 | 0.0 a | 2 | 293.9 a–c | 2 | 1.560 a | 2 | 6.00 a–c | 2 | 3.00 a |
| 40 | 2 | 0.0 a | 2 | 0.0 a | 2 | 334.3 a–b | 2 | 1.321 c | 2 | 4.00 b–e | 2 | 0.25 b |

Portmicin

| | | | | | | | | | | | |
|---|---|---|---|---|---|---|---|---|---|---|---|
| 10 | 2 | 0.0 a | 2 | 0.0 a | 2 | 261.0 c | 2 | 1.544 a | 2 | 8.00 a | 2 | 3.38 a |
| 40 | 2 | 0.0 a | 2 | 0.0 a | 2 | 324.1 a–b | 2 | 1.368 b–c | 2 | 4.25 b–e | 2 | 3.13 a |

Portmicin and Example 1

| | | | | | | | | | | | |
|---|---|---|---|---|---|---|---|---|---|---|---|
| 10 + 10 | 2 | 12.5 a | 2 | 12.5 a | 2 | 313.0 a–b | 2 | 1.517 a–b | 2 | 6.25 a–b | 2 | 2.63 a |
| 20 + 20 | 2 | 0.0 a | 2 | 0.0 a | 2 | 330.8 a–b | 2 | 1.371 b–c | 2 | 3.13 c–e | 2 | 0.50 b |
| 40 + 40 | 2 | 0.0 a | 2 | 0.0 a | 2 | 321.9 a–b | 2 | 1.327 c | 2 | 1.38 e–f | 2 | 0.00 b |
| Salinomycin 66 | 2 | 0.0 a | 2 | 0.0 a | 2 | 295.6 a–c | 2 | 1.449 a–c | 2 | 5.25 a–d | 2 | 3.25 a |
| Maxiban ® 100 | 2 | 0.0 a | 2 | 0.0 a | 2 | 350.0 a | 2 | 1.309 c | 2 | 2.38 d–f | 2 | 0.63 b |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 10 | 28.4 | 10 | 28.4 | 10 | 1397.3 | 10 | 0.022 | 10 | 12.03 | 10 | 4.83 |
| Error | 11 | 28.4 | 11 | 28.4 | 11 | 237.9 | 11 | 0.003 | 11 | 0.81 | 11 | 0.23 |

TABLE 6

Inoculated with *E. adenoeides*, and *E. meleagrimitis*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 2 | 0.0 a | 2 | 0.0 a | 2 | 139.6 a | 2 | 1.780 b | 2 | 0.25 b | 2 | 0.00 c |
| IC 0 | 2 | 0.0 a | 2 | 0.0 a | 2 | 84.6 b | 2 | 2.215 b | 2 | 8.25 a | 2 | 2.25 a–b |

Portmicin

| | | | | | | | | | | | |
|---|---|---|---|---|---|---|---|---|---|---|---|
| 20 | 2 | 0.0 a | 2 | 0.0 a | 2 | 78.1 b | 2 | 2.142 b | 2 | 0.00 b | 2 | 0.00 c |
| 40 | 2 | 0.0 a | 2 | 0.0 a | 2 | 44.6 c | 2 | 3.067 a | 2 | 0.75 b | 2 | 0.00 c |

Example 1

| | | | | | | | | | | | |
|---|---|---|---|---|---|---|---|---|---|---|---|
| 20 | 2 | 0.0 a | 2 | 0.0 a | 2 | 87.3 b | 2 | 2.264 b | 2 | 6.50 a | 2 | 1.50 b–c |
| 40 | 2 | 0.0 a | 2 | 0.0 a | 2 | 100.8 b | 2 | 1.841 b | 2 | 7.00 a | 2 | 3.25 a |

Portmicin and Example 1

| | | | | | | | | | | | |
|---|---|---|---|---|---|---|---|---|---|---|---|
| 20 + 20 | 2 | 0.0 a | 2 | 0.0 a | 2 | 94.8 b | 2 | 1.838 b | 2 | 0.75 b | 2 | 0.00 c |
| 40 + 40 | 2 | 0.0 a | 2 | 0.0 a | 2 | 105.1 b | 2 | 1.705 b | 2 | 1.50 b | 2 | 0.00 c |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 7 | 0.0 | 7 | 0.0 | 7 | 1441.1 | 7 | 0.392 | 7 | 24.18 | 7 | 3.36 |
| Error | 8 | 0.0 | 8 | 0.0 | 8 | 165.3 | 8 | 0.050 | 8 | 1.31 | 8 | 0.22 |

TABLE 7

Inoculated with *E. tenella* and *E. aervulina*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 2 | 0.0 a | 2 | 0.0 a | 2 | 246.0 a | 2 | 1.362 a | 2 | 0.00 c | 2 | 0.00 c |
| IC | 2 | 0.0 a | 2 | 0.0 a | 2 | 158.8 a | 2 | 1.766 a | 2 | 9.17 a | 2 | 3.33 a |

TABLE 7-continued

Inoculated with *E. tenella* and *E. aervulina*

Example 11

| | | | | | | | | | | | | | |
|---|---|---|---|---|---|---|---|---|---|---|---|---|---|
| 25  | 2 | 0.0 a  | 2 | 0.0 a  | 2 | 196.0 a | 2 | 1.595 a | 2 | 7.33 a–b | 2 | 3.00 a |
| 50  | 2 | 16.7 a | 2 | 16.7 a | 2 | 189.1 a | 2 | 1.562 a | 2 | 7.17 a–b | 2 | 4.00 a |
| 100 | 2 | 0.0 a  | 2 | 0.0 a  | 2 | 230.3 a | 2 | 1.400 a | 2 | 4.00 b–c | 2 | 1.83 b |

Example 13

| | | | | | | | | | | | | | |
|---|---|---|---|---|---|---|---|---|---|---|---|---|---|
| 25  | 2 | 0.0 a  | 2 | 0.0 a  | 2 | 188.5 a | 2 | 1.627 a | 2 | 7.83 a–b | 2 | 3.67 a |
| 50  | 2 | 16.7 a | 2 | 16.7 a | 2 | 177.3 a | 2 | 2.050 a | 2 | 8.75 a–b | 2 | 3.75 a |
| 100 | 2 | 0.0 a  | 2 | 0.0 a  | 2 | 177.6 a | 2 | 1.639 a | 2 | 7.50 a–b | 2 | 3.33 b |

Example 1

| | | | | | | | | | | | | | |
|---|---|---|---|---|---|---|---|---|---|---|---|---|---|
| 25  | 2 | 16.7 a | 2 | 16.7 a | 2 | 228.4 a | 2 | 1.541 a | 2 | 7.17 a–b | 2 | 3.67 a |
| 50  | 2 | 0.0 a  | 2 | 0.0 a  | 2 | 235.7 a | 2 | 1.349 a | 2 | 1.83 c   | 2 | 1.33 b |
| 100 | 2 | 0.0 a  | 2 | 0.0 a  | 2 | 229.4 a | 2 | 1.375 a | 2 | 0.00 c   | 2 | 0.00 c |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 10 | 121.2 | 10 | 90.9  | 10 | 1734.5 | 10 | 0.087 | 10 | 23.71 | 10 | 4.49 |
| Error  | 11 | 151.5 | 11 | 101.0 | 11 | 517.4  | 11 | 0.042 | 11 | 1.96  | 11 | 0.24 |

TABLE 8

Inoculated with *E. maxima* and *E. tenella*

| Treatment | Mortality | | Mean | | Wt. Gain | | Feed/Gain | | Lesion Scores — Intestinal | | Lesion Scores — Cecal | |
|---|---|---|---|---|---|---|---|---|---|---|---|---|
| PPM | # | Total % | # | % DTC | # | Mean | # | Mean | # | Mean | # | Mean |
| NC 0 | 4 | 0.0 d | 4 | 0.0 d | 4 | 353.7 a | 4 | 1.346 c | 4 | 0.00 d | 4 | 0.00 d |
| IC 0 | 4 | 25.0 a–c | 4 | 25.0 a | 4 | 186.6 e–f | 4 | 2.187 a | 4 | 8.63 a | 4 | 3.13 a |
| Portmicin | | | | | | | | | | | | |
| 15 | 4 | 31.3 a | 4 | 31.3 a | 4 | 157.1 f   | 4 | 2.241 a | 4 | 8.88 a | 4 | 3.75 a |
| 30 | 4 | 0.0 d  | 4 | 0.0 d  | 4 | 255.6 b–d | 4 | 1.681 b–c | 4 | 7.69 a | 4 | 2.94 a |
| 45 | 4 | 0.0 d  | 4 | 0.0 d  | 4 | 288.6 a–c | 4 | 1.561 b–c | 4 | 5.50 b | 4 | 3.13 a |
| 60 | 4 | 0.0 d  | 4 | 0.0 d  | 4 | 307.5 a–c | 4 | 1.474 b–c | 4 | 1.38 d | 4 | 1.44 b |
| Example 1 | | | | | | | | | | | | |
| 15 | 4 | 31.3 a   | 4 | 12.5 b | 4 | 219.9 d–e | 4 | 2.115 a   | 4 | 9.00 a | 4 | 3.21 a |
| 30 | 4 | 12.5 a–d | 4 | 0.0 d  | 4 | 285.1 a–c | 4 | 1.632 b–c | 4 | 8.44 a | 4 | 1.42 b |
| 45 | 4 | 0.0 d    | 4 | 0.0 d  | 4 | 322.7 a–c | 4 | 1.376 b–c | 4 | 3.13 c | 4 | 0.06 d |
| 60 | 4 | 12.5 a–d | 4 | 0.0 d  | 4 | 314.2 a–c | 4 | 1.479 b–c | 4 | 0.90 d | 4 | 0.00 d |
| Portmicin and Example 1 | | | | | | | | | | | | |
| 15 + 15 | 4 | 0.0 d    | 4 | 0.0 d | 4 | 317.8 a–c | 4 | 1.411 b–c | 4 | 3.13 c | 4 | 1.19 b–c |
| 15 + 30 | 4 | 6.3 a–d  | 4 | 0.0 d | 4 | 322.8 a–c | 4 | 1.425 b–c | 4 | 0.23 d | 4 | 0.21 d |
| 15 + 45 | 4 | 0.0 d    | 4 | 0.0 d | 4 | 330.5 a–c | 4 | 1.419 b–c | 4 | 0.00 d | 4 | 0.00 d |
| 15 + 60 | 4 | 6.3 a–d  | 4 | 0.0 d | 4 | 321.9 a–c | 4 | 1.451 b–c | 4 | 0.06 d | 4 | 0.13 d |
| 30 + 15 | 4 | 0.0 d    | 4 | 0.0 d | 4 | 329.0 a–c | 4 | 1.438 b–c | 4 | 0.75 d | 4 | 0.63 c–d |
| 30 + 30 | 4 | 0.0 d    | 4 | 0.0 d | 4 | 326.1 a–c | 4 | 1.417 b–c | 4 | 0.00 d | 4 | 0.00 d |
| 30 + 45 | 4 | 0.0 d    | 4 | 0.0 d | 4 | 323.4 a–c | 4 | 1.455 b–c | 4 | 0.06 d | 4 | 0.00 d |
| 30 + 60 | 4 | 0.0 d    | 4 | 0.0 d | 4 | 308.1 a–c | 4 | 1.432 b–c | 4 | 0.13 d | 4 | 0.00 d |
| 45 + 15 | 4 | 0.0 d    | 4 | 0.0 d | 4 | 341.5 a   | 4 | 1.357 c   | 4 | 0.19 d | 4 | 0.00 d |
| 45 + 30 | 4 | 6.3 a–d  | 4 | 0.0 d | 4 | 327.5 a–c | 4 | 1.417 b–c | 4 | 0.00 d | 4 | 0.00 d |
| 45 + 45 | 4 | 12.5 a–d | 4 | 0.0 d | 4 | 333.8 a–b | 4 | 1.432 b–c | 4 | 0.00 d | 4 | 0.00 d |
| 45 + 60 | 4 | 6.3 a–d  | 4 | 0.0 d | 4 | 294.8 a–c | 4 | 1.499 b–c | 4 | 0.00 d | 4 | 0.00 d |
| 60 + 15 | 4 | 6.3 a–d  | 4 | 0.0 d | 4 | 327.1 a–c | 4 | 1.395 b–c | 4 | 0.17 d | 4 | 0.00 d |
| 60 + 30 | 4 | 6.3 a–d  | 4 | 0.0 d | 4 | 317.3 a–c | 4 | 1.441 b–c | 4 | 0.00 d | 4 | 0.00 d |
| 60 + 45 | 4 | 0.0 d    | 4 | 0.0 d | 4 | 290.8 a–c | 4 | 1.506 b–c | 4 | 0.06 d | 4 | 0.00 d |
| 60 + 60 | 4 | 25.0 a–c | 4 | 0.0 d | 4 | 251.4 c–d | 4 | 1.705 b   | 4 | 0.00 d | 4 | 0.00 d |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 25 | 408.7 | 25 | 252.2 | 25 | 9140.4 | 25 | 0.249 | 25 | 45.91 | 25 | 6.58 |
| Error  | 78 | 120.2 | 78 | 30.0  | 78 | 940.3  | 78 | 0.016 | 78 | 0.73  | 78 | 0.18 |

TABLE 9

Inoculated with E. tenella and E. acervulina

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 e | 4 | 0.0 e | 4 | 336.7 a–c | 4 | 382 d–e | 4 | 0.00 e | 4 | 0.00 c |
| IC 0 | 4 | 0.0 e | 4 | 0.0 e | 4 | 275.5 e–f | 4 | 1.623 a–b | 4 | 5.63 a | 4 | 3.13 a |
| Portmicin | | | | | | | | | | | | |
| 15 | 4 | 6.3 a–e | 4 | 0.0 e | 4 | 317.5 a–e | 4 | 1.518 a–e | 4 | 3.31 c | 4 | 3.69 a |
| 30 | 4 | 6.3 a–e | 4 | 6.3 a–b | 4 | 304.5 a–e | 4 | 1.525 a–e | 4 | 1.69 d | 4 | 3.75 a |
| 45 | 4 | 0.0 e | 4 | 0.0 e | 4 | 339.0 a–c | 4 | 1.447 c–e | 4 | 0.44 e | 4 | 2.38 b |
| 60 | 4 | 12.5 a | 4 | 0.0 e | 4 | 306.2 a–e | 4 | 1.521 a–e | 4 | 0.00 e | 4 | 1.96 b |
| Example 1 | | | | | | | | | | | | |
| 15 | 4 | 6.3 a–e | 4 | 6.3 a–b | 4 | 289.2 d–f | 4 | 1.631 a | 4 | 4.56 b | 4 | 3.50 a |
| 30 | 4 | 6.3 a–e | 4 | 0.0 e | 4 | 315.6 a–e | 4 | 1.479 a–e | 4 | 1.13 d–e | 4 | 0.23 c |
| 45 | 4 | 0.0 e | 4 | 0.0 e | 4 | 318.4 a–e | 4 | 1.458 b–e | 4 | 0.00 e | 4 | 0.00 c |
| 60 | 4 | 6.3 a–e | 4 | 0.0 e | 4 | 321.8 a–d | 4 | 1.417 c–e | 4 | 0.00 e | 4 | 0.00 c |
| Portmicin and Example 1 | | | | | | | | | | | | |
| 15 + 15 | 4 | 0.0 e | 4 | 0.0 e | 4 | 331.9 d | 4 | 1.400 d–e | 4 | 0.69 e | 4 | 2.13 b |
| 15 + 30 | 4 | 0.0 e | 4 | 0.0 e | 4 | 349.1 a | 4 | 1.388 d–e | 4 | 0.06 e | 4 | 0.06 c |
| 15 + 45 | 4 | 0.0 e | 4 | 0.0 e | 4 | 341.0 a–b | 4 | 1.390 d–e | 4 | 0.00 e | 4 | 0.00 c |
| 15 + 60 | 4 | 0.0 e | 4 | 0.0 e | 4 | 329.9 a–d | 4 | 1.459 b–e | 4 | 0.00 e | 4 | 0.13 c |
| 30 + 15 | 4 | 0.0 e | 4 | 0.0 e | 4 | 350.1 e | 4 | 1.354 e | 4 | 0.00 e | 4 | 0.38 c |
| 30 + 30 | 4 | 0.0 e | 4 | 0.0 e | 4 | 330.2 a–d | 4 | 1.436 c–e | 4 | 0.00 e | 4 | 0.00 c |
| 30 + 45 | 4 | 0.0 e | 4 | 0.0 e | 4 | 322.7 a–d | 4 | 1.364 e | 4 | 0.00 e | 4 | 0.00 c |
| 30 + 60 | 4 | 6.3 a–e | 4 | 0.0 e | 4 | 312.9 a–e | 4 | 1.472 a–e | 4 | 0.00 e | 4 | 0.00 c |
| 45 + 15 | 4 | 6.3 a–e | 4 | 0.0 e | 4 | 326.7 a–d | 4 | 1.378 d–e | 4 | 0.00 e | 4 | 0.00 c |
| 45 + 30 | 4 | 0.0 e | 4 | 0.0 e | 4 | 333.1 a–d | 4 | 1.397 d–e | 4 | 0.00 e | 4 | 0.00 c |
| 45 + 45 | 4 | 0.0 e | 4 | 0.0 e | 4 | 328.0 a–d | 4 | 1.406 d–e | 4 | 0.00 e | 4 | 0.00 c |
| 45 + 60 | 4 | 6.3 a–e | 4 | 0.0 e | 4 | 294.3 b–d | 4 | 1.518 a–e | 4 | 0.00 e | 4 | 0.00 c |
| 60 + 15 | 4 | 0.0 e | 4 | 0.0 e | 4 | 313.5 a–e | 4 | 1.430 c–e | 4 | 0.00 e | 4 | 0.00 c |
| 60 + 30 | 4 | 0.0 e | 4 | 0.0 e | 4 | 313.2 a–e | 4 | 1.435 c–e | 4 | 0.00 e | 4 | 0.13 c |
| 60 + 45 | 4 | 0.0 e | 4 | 0.0 e | 4 | 292.8 c–f | 4 | 1.552 a–d | 4 | 0.00 e | 4 | 0.00 c |
| 60 + 60 | 4 | 0.0 e | 4 | 0.0 e | 4 | 264.3 f | 4 | 1.589 a–c | 4 | 0.00 e | 4 | 0.00 c |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 25 | 51.0 | 25 | 11.5 | 25 | 1817.0 | 25 | 0.025 | 25 | 9.03 | 25 | 7.40 |
| Error | 78 | 56.1 | 78 | 12.0 | 78 | 323.7 | 78 | 0.005 | 78 | 0.34 | 78 | 0.13 |

TABLE 10

Inoculated with E. tenella and E. acervulina

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 e | 4 | 0.0 d | 4 | 349.5 a | 4 | 1.374 e | 4 | 0.00 d | 4 | 0.00 e |
| IC 0 | 4 | 18.8 a–c | 4 | 12.5 a | 4 | 218.1 f | 4 | 1.867 a | 4 | 8.00 a | 4 | 3.48 a |
| Portmicin | | | | | | | | | | | | |
| 15 | 4 | 6.3 a–e | 4 | 0.0 d | 4 | 271.5 c–e | 4 | 1.671 b–d | 4 | 4.48 b | 4 | 2.98 b |
| 30 | 4 | 0.0 e | 4 | 0.0 d | 4 | 328.1 a–b | 4 | 1.455 e | 4 | 0.44 c | 4 | 1.56 c |
| 45 | 4 | 18.8 a–c | 4 | 0.0 d | 4 | 306.7 a–e | 4 | 1.505 c–e | 4 | 0.06 c–d | 4 | 0.13 e |
| 60 | 4 | 6.3 a–e | 4 | 0.0 d | 4 | 339.8 a | 4 | 1.410 e | 4 | 0.00 d | 4 | 0.00 e |
| Example 1 | | | | | | | | | | | | |
| 15 | 4 | 12.5 a–e | 4 | 12.5 a | 4 | 257.6 e | 4 | 1.729 b | 4 | 5.00 b | 4 | 3.69 a |
| 30 | 4 | 0.0 e | 4 | 0.0 d | 4 | 322.9 a–c | 4 | 1.480 d–e | 4 | 0.19 c–d | 4 | 1.00 d |
| 45 | 4 | 6.3 a–e | 4 | 0.0 d | 4 | 304.9 a–e | 4 | 1.455 e | 4 | 0.00 d | 4 | 0.00 e |
| 60 | 4 | 0.0 e | 4 | 0.0 d | 4 | 297.4 a–e | 4 | 1.452 e | 4 | 0.00 d | 4 | 0.00 e |

TABLE 10-continued

Inoculated with E. tenella and E. acervulina

Portmicin and Example 1

| | | | | | | | | | | | |
|---|---|---|---|---|---|---|---|---|---|---|---|
| 15 + 15 | | 4 | 0.0 e | 4 | 0.0 d | 4 | 342.7 a | 4 | 1.421 e | 4 | 0.38 c–d | 4 | 0.25 e |
| 15 + 30 | | 4 | 6.3 a–e | 4 | 0.0 d | 4 | 331.5 a–b | 4 | 1.436 e | 4 | 0.00 d | 4 | 0.08 e |
| 15 + 45 | | 4 | 6.3 a–e | 4 | 0.0 d | 4 | 327.6 a–b | 4 | 1.509 c–e | 4 | 0.00 d | 4 | 0.00 e |
| 15 + 60 | | 4 | 6.3 a–e | 4 | 0.0 d | 4 | 300.2 a–e | 4 | 1.514 c–e | 4 | 0.00 d | 4 | 0.00 e |
| 30 + 15 | | 4 | 6.3 a–e | 4 | 0.0 d | 4 | 343.9 a | 4 | 1.427 e | 4 | 0.00 d | 4 | 0.00 e |
| 30 + 30 | | 4 | 0.0 e | 4 | 0.0 d | 4 | 327.7 a–b | 4 | 1.417 e | 4 | 0.00 d | 4 | 0.00 e |
| 30 + 45 | | 4 | 6.3 a–e | 4 | 0.0 d | 4 | 299.9 a–e | 4 | 1.548 c–e | 4 | 0.00 d | 4 | 0.00 e |
| 30 + 60 | | 4 | 0.0 e | 4 | 0.0 d | 4 | 281.1 b–e | 4 | 1.563 b–e | 4 | 0.00 d | 4 | 0.00 e |
| 45 + 15 | | 4 | 6.3 a–e | 4 | 0.0 d | 4 | 307.5 a–e | 4 | 1.524 c–e | 4 | 0.00 d | 4 | 0.00 e |
| 45 + 30 | | 4 | 0.0 e | 4 | 0.0 d | 4 | 330.8 a–b | 4 | 1.385 e | 4 | 0.00 d | 4 | 0.00 e |
| 45 + 45 | | 4 | 12.5 a–e | 4 | 0.0 d | 4 | 298.4 a–e | 4 | 1.588 b–e | 4 | 0.00 d | 4 | 0.00 e |
| 45 + 60 | | 4 | 6.3 a–e | 4 | 0.0 d | 4 | 295.2 a–e | 4 | 1.507 c–e | 4 | 0.00 d | 4 | 0.00 e |
| 60 + 15 | | 4 | 6.3 a–e | 4 | 0.0 d | 4 | 314.2 a–c | 4 | 1.497 c–e | 4 | 0.00 d | 4 | 0.0 e |
| 60 + 30 | | 4 | 0.0 e | 4 | 0.0 d | 4 | 308.5 a–e | 4 | 1.439 e | 4 | 0.00 d | 4 | 0.00 e |
| 60 + 45 | | 4 | 6.3 a–e | 4 | 0.0 d | 4 | 309.6 a–e | 4 | 1.482 d–e | 4 | 0.00 d | 4 | 0.00 e |
| 60 + 60 | | 4 | 18.8 a–c | 4 | 0.0 d | 4 | 262.7 d–e | 4 | 1.696 b–c | 4 | 0.00 d | 4 | 0.00 e |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 25 | 143.5 | 25 | 46.2 | 25 | 3667.8 | 25 | 0.054 | 25 | 15.39 | 25 | 5.03 |
| Error | 78 | 138.2 | 78 | 16.0 | 78 | 479.6 | 78 | 0.007 | 78 | 0.17 | 78 | 0.12 |

TABLE 11

Inoculated with E. tenella and E. maxima

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 e | 4 | 0.0 e | 4 | 359.4 a | 4 | 1.330 d | 4 | 0.63 c | 4 | 0.00 d |
| IC 0 | 4 | 43.8 a | 4 | 37.5 a | 4 | 181.0 e | 4 | 2.198 a | 4 | 8.50 a | 4 | 3.83 a |
| Portmicin | | | | | | | | | | | | |
| 15 | 4 | 6.3 b–e | 4 | 6.3 b | 4 | 250.5 d | 4 | 1.694 b | 4 | 7.50 a | 4 | 3.06 b |
| 30 | 4 | 6.3 b–e | 4 | 0.0 e | 4 | 336.5 b–c | 4 | 1.460 c–d | 4 | 0.94 c | 4 | 0.25 c–d |
| 45 | 4 | 0.0 e | 4 | 0.0 e | 4 | 342.4 a–c | 4 | 1.409 d | 4 | 1.19 c | 4 | 0.25 c–d |
| 60 | 4 | 0.0 e | 4 | 0.0 e | 4 | 337.0 a–c | 4 | 1.398 d | 4 | 0.00 c | 4 | 0.0 d |
| Example 1 | | | | | | | | | | | | |
| 15 | 4 | 0.0 e | 4 | 0.0 e | 4 | 260.0 d | 4 | 1.615 b–c | 4 | 8.44 a | 4 | 3.31 b |
| 30 | 4 | 0.0 e | 4 | 0.0 e | 4 | 321.3 a–c | 4 | 1.387 d | 4 | 4.06 b | 4 | 0.19 c–d |
| 45 | 4 | 12.5 b–c | 4 | 0.0 e | 4 | 334.3 a–c | 4 | 1.442 c–d | 4 | 0.00 c | 4 | 0.00 d |
| 60 | 4 | 0.0 e | 4 | 0.0 e | 4 | 300.1 b–c | 4 | 1.467 c–d | 4 | 0.25 c | 4 | 0.00 d |
| Portmicin and Example 1 | | | | | | | | | | | | |
| 15 + 15 | 4 | 0.0 e | 4 | 0.0 e | 4 | 354.3 a–b | 4 | 1.379 d | 4 | 0.06 c | 4 | 0.00 d |
| 15 + 30 | 4 | 0.0 e | 4 | 0.0 e | 4 | 353.9 a–b | 4 | 1.346 d | 4 | 0.06 c | 4 | 0.00 d |
| 15 + 45 | 4 | 0.0 e | 4 | 0.0 e | 4 | 349.9 a–c | 4 | 1.336 d | 4 | 0.00 c | 4 | 0.00 d |
| 15 + 60 | 4 | 0.0 e | 4 | 0.0 e | 4 | 307.9 a–c | 4 | 1.461 c–d | 4 | 0.00 c | 4 | 0.00 d |
| 30 + 15 | 4 | 0.0 e | 4 | 0.0 e | 4 | 349.8 a–c | 4 | 1.307 d | 4 | 0.19 | 4 | 0.0 d |
| 30 + 30 | 4 | 0.0 e | 4 | 0.0 e | 4 | 347.2 a–c | 4 | 1.370 d | 4 | 0.00 c | 4 | 0.00 d |
| 30 + 45 | 4 | 6.3 b–e | 4 | 0.0 e | 4 | 342.0 a–c | 4 | 1.408 d | 4 | 0.00 c | 4 | 0.00 d |
| 30 + 60 | 4 | 0.0 e | 4 | 0.0 e | 4 | 316.9 a–c | 4 | 1.443 c–d | 4 | 0.00 c | 4 | 0.00 d |
| 45 + 15 | 4 | 0.0 e | 4 | 0.0 e | 4 | 341.4 a–c | 4 | 1.390 d | 4 | 0.00 c | 4 | 0.00 d |
| 45 + 30 | 4 | 0.0 e | 4 | 0.0 e | 4 | 334.0 a–c | 4 | 1.354 d | 4 | 0.06 c | 4 | 0.00 d |
| 45 + 45 | 4 | 0.0 e | 4 | 0.0 e | 4 | 305.5 a–c | 4 | 1.477 c–d | 4 | 1.13 c | 4 | 0.25 c–d |
| 45 + 60 | 4 | 0.0 e | 4 | 0.0 e | 4 | 293.0 c | 4 | 1.508 c–d | 4 | 0.00 c | 4 | 0.00 d |
| 60 + 15 | 4 | 0.0 e | 4 | 0.0 e | 4 | 308.2 a–c | 4 | 1.481 c–d | 4 | 0.00 c | 4 | 0.00 d |
| 60 + 30 | 4 | 6.3 b–e | 4 | 0.0 e | 4 | 329.2 a–c | 4 | 1.437 d | 4 | 0.00 c | 4 | 0.00 d |
| 60 + 45 | 4 | 12.5 b–c | 4 | 0.0 e | 4 | 310.4 a–c | 4 | 1.475 c–d | 4 | 0.08 c | 4 | 0.00 d |
| 60 + 60 | 4 | 6.3 b–e | 4 | 0.0 e | 4 | 253.1 d | 4 | 1.673 b | 4 | 0.00 c | 4 | 0.00 d |

TABLE 11-continued

Inoculated with *E. tenella* and *E. maxima*

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 25 | 326.0 | 25 | 219.5 | 25 | 6792.7 | 25 | 0.126 | 25 | 28.51 | 25 | 4.88 |
| Error | 78 | 52.1 | 78 | 14.0 | 78 | 488.2 | 78 | 0.007 | 78 | 0.48 | 78 | 0.06 |

TABLE 12

Inoculated with *E. tenella* and *E. acervulina*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 d | 4 | 0.0 d | 4 | 353.7 a | 4 | 1.346 c | 4 | 0.00 d | 4 | 0.00 d |
| IC 0 | 4 | 25.0 a–c | 4 | 25.0 a | 4 | 186.6 e–f | 4 | 2.187 a | 4 | 8.63 a | 4 | 3.13 a |
| Portmicin and Example 1 | | | | | | | | | | | | |
| 15 + 15 | 4 | 0.0 a | 4 | 0.0 a | 4 | 279.8 a | 4 | 1.391 b–c | 4 | 0.00 b | 4 | 0.00 b |
| 20 + 20 | 4 | 0.0 a | 4 | 0.0 a | 4 | 280.0 a | 4 | 1.447 b–c | 4 | 0.00 b | 4 | 0.19 b |
| 25 + 25 | 4 | 0.0 a | 4 | 0.0 a | 4 | 278.2 a | 4 | 1.428 b–c | 4 | 0.00 b | 4 | 0.00 b |
| 30 + 30 | 4 | 0.0 a | 4 | 0.0 a | 4 | 282.7 a | 4 | 1.372 b–c | 4 | 0.00 b | 4 | 0.13 b |
| 35 + 35 | 4 | 0.0 a | 4 | 0.0 a | 4 | 268.3 a | 4 | 1.415 b–c | 4 | 0.00 b | 4 | 0.00 b |
| 40 + 40 | 4 | 0.0 a | 4 | 0.0 a | 4 | 258.6 a–b | 4 | 1.433 b–c | 4 | 0.00 b | 4 | 0.00 b |
| 20 + 10 | 4 | 0.0 a | 4 | 0.0 a | 4 | 279.6 a | 4 | 1.364 b–c | 4 | 0.06 b | 4 | 0.00 b |
| 26.7 + 13.3 | 4 | 6.3 a | 4 | 0.0 a | 4 | 291.5 a | 4 | 1.393 b–c | 4 | 0.00 b | 4 | 0.00 b |
| 33.4 + 16.7 | 4 | 6.3 a | 4 | 0.0 a | 4 | 280.3 a | 4 | 1.315 b–c | 4 | 0.00 b | 4 | 0.00 b |
| 40 + 20 | 4 | 0.0 a | 4 | 0.0 a | 4 | 253.6 a–b | 4 | 1.471 b–c | 4 | 0.00 b | 4 | 0.00 b |
| 46.7 + 23.3 | 4 | 0.0 a | 4 | 0.0 a | 4 | 252.4 a–b | 4 | 1.446 b–c | 4 | 0.00 b | 4 | 0.00 b |
| 53.4 + 26.6 | 4 | 0.0 a | 4 | 0.0 a | 4 | 219.9 a–b | 4 | 1.644 b | 4 | 0.00 b | 4 | 0.00 b |
| 22.5 + 7.5 | 4 | 0.0 a | 4 | 0.0 a | 4 | 292.9 a | 4 | 1.311 c | 4 | 0.00 b | 4 | 0.00 b |
| 30 + 10 | 4 | 0.0 a | 4 | 0.0 a | 4 | 286.1 a | 4 | 1.368 b–c | 4 | 0.00 b | 4 | 0.06 b |
| 37.5 + 12.5 | 4 | 0.0 a | 4 | 0.0 a | 4 | 270.9 a | 4 | 1.376 b–c | 4 | 0.06 b | 4 | 0.00 b |
| 45 + 15 | 4 | 0.0 a | 4 | 0.0 a | 4 | 271.7 a | 4 | 1.404 b–c | 4 | 0.00 b | 4 | 0.00 b |
| 52.5 + 17.5 | 4 | 0.0 a | 4 | 0.0 a | 4 | 263.7 a–b | 4 | 1.407 b–c | 4 | 0.00 b | 4 | 0.00 b |
| 60 + 20 | 4 | 0.0 a | 4 | 0.0 a | 4 | 234.7 a–b | 4 | 1.565 b–c | 4 | 0.00 b | 4 | 0.00 b |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 19 | 47.3 | 19 | 7.8 | 19 | 2344.9 | 19 | 0.088 | 19 | 12.59 | 19 | 2.21 |
| Error | 60 | 33.9 | 60 | 7.8 | 60 | 801.6 | 60 | 0.016 | 60 | 0.00 | 60 | 0.02 |

TABLE 13

Inoculated with *E. tenella* and *E. acervulina*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 a | 4 | 0.0 a | 4 | 316.3 a | 4 | 1.299 c | 4 | 0.00 c | 4 | 0.00 f |
| IC 0 | 4 | 12.5 a | 4 | 12.5 a | 4 | 196.6 b | 4 | 1.808 a | 4 | 7.63 a | 4 | 3.69 a |
| Portmicin and Example 1 | | | | | | | | | | | | |
| 15 + 15 | 4 | 12.5 a | 4 | 6.3 a | 4 | 315.9 a | 4 | 1.374 b–c | 4 | 2.33 b | 4 | 3.08 a–b |
| 20 + 20 | 4 | 0.0 a | 4 | 0.0 a | 4 | 319.2 a | 4 | 1.304 c | 4 | 0.44 c | 4 | 1.19 d–f |
| 25 + 25 | 4 | 0.0 a | 4 | 0.0 a | 4 | 313.0 a | 4 | 1.310 c | 4 | 0.06 c | 4 | 0.38 f |
| 30 + 30 | 4 | 6.3 a | 4 | 0.0 a | 4 | 311.0 a | 4 | 1.328 b–c | 4 | 0.00 c | 4 | 0.00 f |
| 35 + 35 | 4 | 0.0 a | 4 | 0.0 a | 4 | 322.3 a | 4 | 1.370 b–c | 4 | 0.00 c | 4 | 0.00 f |
| 40 + 40 | 4 | 0.0 a | 4 | 0.0 a | 4 | 306.3 a | 4 | 1.314 c | 4 | 0.00 c | 4 | 0.00 f |
| 20 + 10 | 4 | 6.3 a | 4 | 0.0 a | 4 | 298.5 a | 4 | 1.394 b–c | 4 | 2.06 b | 4 | 2.94 a–b |
| 26.7 + 13.3 | 4 | 0.0 a | 4 | 0.0 a | 4 | 312.8 a | 4 | 1.310 c | 4 | 0.38 c | 4 | 1.81 c–e |

TABLE 13-continued

Inoculated with *E. tenella* and *E. acervulina*

| | | | | | | | | | | | | |
|---|---|---|---|---|---|---|---|---|---|---|---|---|
| 33.4 + 16.7 | | 4 | 0.0 a | 4 | 0.0 a | 4 | 328.9 a | 4 | 1.323 b-c | 4 | 0.13 c | 4 | 0.19 f |
| 40 + 20 | | 4 | 6.3 a | 4 | 0.0 a | 4 | 306.1 a | 4 | 1.335 b-c | 4 | 0.06 c | 4 | 0.35 f |
| 46.7 + 23.3 | | 4 | 0.0 a | 4 | 0.0 a | 4 | 308.8 a | 4 | 1.348 b-c | 4 | 0.06 c | 4 | 0.13 f |
| 53.4 + 26.6 | | 4 | 0.0 a | 4 | 0.0 a | 4 | 308.8 a | 4 | 1.317 b-c | 4 | 0.00 c | 4 | 0.00 f |
| 22.5 + 7.5 | | 4 | 0.0 a | 4 | 0.0 a | 4 | 287.9 a | 4 | 1.504 b | 4 | 2.63 b | 4 | 3.38 a |
| 30 + 10 | | 4 | 0.0 a | 4 | 0.0 a | 4 | 325.3 a | 4 | 1.321 b-c | 4 | 0.69 c | 4 | 2.31 b-c |
| 37.5 + 12.5 | | 4 | 0.0 a | 4 | 0.0 a | 4 | 299.6 a | 4 | 1.364 b-c | 4 | 0.31 c | 4 | 2.13 b-d |
| 45 + 15 | | 4 | 0.0 a | 4 | 0.0 a | 4 | 323.0 a | 4 | 1.292 c | 4 | 0.13 c | 4 | 1.00 e-f |
| 52.5 + 17.5 | | 4 | 0.0 a | 4 | 0.0 a | 4 | 308.6 a | 4 | 1.377 b-c | 4 | 0.00 c | 4 | 0.00 f |
| 60 + 20 | | 4 | 0.0 a | 4 | 0.0 a | 4 | 300.5 a | 4 | 1.317 b-c | 4 | 0.06 c | 4 | 0.00 f |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 19 | 70.3 | 19 | 37.4 | 19 | 3028.1 | 19 | 0.053 | 19 | 12.91 | 19 | 7.06 |
| Error | 60 | 65.1 | 60 | 39.1 | 60 | 523.0 | 60 | 0.006 | 60 | 0.20 | 60 | 0.31 |

TABLE 14

Inoculated with *E. tenella*, *E. acervulina* and *E. maxima*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 12.5 a | 4 | 0.0 a | 4 | 306.6 a | 4 | 1.456 a | 4 | 0.00 f | 4 | 0.00 e |
| IC 0 | 4 | 6.3 a | 4 | 0.0 a | 4 | 291.7 a | 4 | 1.454 a | 4 | 5.88 a-c | 4 | 2.81 a-b |
| Portmicin and Example 1 | | | | | | | | | | | | |
| 15 + 15 | 4 | 0.0 a | 4 | 0.0 a | 4 | 299.4 a | 4 | 1.388 a | 4 | 4.69 a-d | 4 | 1.75 b-d |
| 20 + 20 | 4 | 0.0 a | 4 | 0.0 a | 4 | 309.1 a | 4 | 1.355 a | 4 | 4.19 a-e | 4 | 2.00 a-c |
| 25 + 25 | 4 | 0.0 a | 4 | 0.0 a | 4 | 281.4 a | 4 | 1.484 a | 4 | 1.44 e-f | 4 | 0.25 d-e |
| 30 + 30 | 4 | 0.0 a | 4 | 0.0 a | 4 | 312.9 a | 4 | 1.390 a | 4 | 2.00 d-f | 4 | 0.44 c-e |
| 35 + 35 | 4 | 6.3 a | 4 | 0.0 a | 4 | 306.4 a | 4 | 1.400 a | 4 | 1.29 e-f | 4 | 0.31 d-e |
| 40 + 40 | 4 | 0.0 a | 4 | 0.0 a | 4 | 300.0 a | 4 | 1.359 a | 4 | 1.13 e-f | 4 | 0.00 e |
| 20 + 10 | 4 | 6.3 a | 4 | 0.0 a | 4 | 301.3 a | 4 | 1.421 a | 4 | 2.60 d-f | 4 | 2.00 a-c |
| 26.7 + 13.3 | 4 | 6.3 a | 4 | 0.0 a | 4 | 300.1 a | 4 | 1.485 a | 4 | 3.69 b-e | 4 | 2.71 a-b |
| 33.4 + 16.7 | 4 | 0.0 a | 4 | 0.0 a | 4 | 312.0 a | 4 | 1.388 a | 4 | 3.94 b-e | 4 | 1.56 b-e |
| 40 + 20 | 4 | 0.0 a | 4 | 0.0 a | 4 | 310.3 a | 4 | 1.362 a | 4 | 2.31 d-f | 4 | 0.69 c-e |
| 46.7 + 23.3 | 4 | 6.3 a | 4 | 0.0 a | 4 | 305.0 a | 4 | 1.383 a | 4 | 2.46 d-f | 4 | 0.54 c-e |
| 53.4 + 26.6 | 4 | 0.0 a | 4 | 0.0 a | 4 | 303.3 a | 4 | 1.420 a | 4 | 2.31 d-f | 4 | 0.56 c-e |
| 22.5 + 7.5 | 4 | 0.0 a | 4 | 0.0 a | 4 | 271.6 a | 4 | 1.493 a | 4 | 6.69 a | 4 | 2.94 a-b |
| 30 + 10 | 4 | 0.0 a | 4 | 0.0 a | 4 | 301.6 a | 4 | 1.413 a | 4 | 6.31 a-b | 4 | 3.38 a |
| 37.5 + 12.5 | 4 | 0.0 a | 4 | 0.0 a | 4 | 283.4 a | 4 | 1.485 a | 4 | 3.63 b-e | 4 | 2.38 a-b |
| 45 + 15 | 4 | 6.3 a | 4 | 0.0 a | 4 | 284.1 a | 4 | 1.415 a | 4 | 3.17 c-e | 4 | 1.63 b-d |
| 52.5 + 17.5 | 4 | 12.5 a | 4 | 0.0 a | 4 | 307.1 a | 4 | 1.459 a | 4 | 2.90 d-f | 4 | 0.88 c-e |
| 60 + 20 | 4 | 0.0 a | 4 | 0.0 a | 4 | 293.1 a | 4 | 1.364 a | 4 | 1.88 d-f | 4 | 0.56 c-e |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 19 | 74.0 | 19 | 0.0 | 19 | 516.0 | 19 | 0.009 | 19 | 12.65 | 19 | 4.65 |
| Error | 60 | 88.5 | 60 | 0.0 | 60 | 610.9 | 60 | 0.010 | 60 | 1.64 | 60 | 0.45 |

TABLE 15

Inoculated with *E. tenella* and *E. maxima*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 b | 4 | 0.0 b | 4 | 326.7 a | 4 | 1.415 b | 4 | 0.13 c | 4 | 0.00 d |

TABLE 15-continued

| Inoculated with E. tenella and E. maxima | | | | | | | | | | | | |
|---|---|---|---|---|---|---|---|---|---|---|---|---|
| IC 0 | | 4 | 25.0 a | 4 | 25.0 a | 4 | 185.1 b | 4 | 2.283 a | 4 | 9.13 a | 4 | 3.81 a |

Portmicin and Example 1

| | | | | | | | | | | | | |
|---|---|---|---|---|---|---|---|---|---|---|---|---|
| 15 + 15 | | 4 | 0.0 b | 4 | 0.0 b | 4 | 308.6 a | 4 | 1.414 b | 4 | 0.94 c | 4 | 0.81 d |
| 20 + 20 | | 4 | 0.0 b | 4 | 0.0 b | 4 | 324.2 a | 4 | 1.417 b | 4 | 0.00 c | 4 | 0.00 d |
| 25 + 25 | | 4 | 0.0 b | 4 | 0.0 b | 4 | 315.4 a | 4 | 1.378 b | 4 | 0.00 c | 4 | 0.00 d |
| 30 + 30 | | 4 | 0.0 b | 4 | 0.0 b | 4 | 304.4 a | 4 | 1.416 b | 4 | 0.00 c | 4 | 0.00 d |
| 35 + 35 | | 4 | 0.0 b | 4 | 0.0 b | 4 | 305.0 a | 4 | 1.460 b | 4 | 0.00 c | 4 | 0.00 d |
| 40 + 40 | | 4 | 0.0 b | 4 | 0.0 b | 4 | 296.5 a | 4 | 1.429 b | 4 | 0.00 c | 4 | 0.00 d |
| 20 + 10 | | 4 | 0.0 b | 4 | 0.0 b | 4 | 323.2 a | 4 | 1.415 b | 4 | 1.25 c | 4 | 1.81 d |
| 26.7 + 13.3 | | 4 | 0.0 b | 4 | 0.0 b | 4 | 297.3 a | 4 | 1.446 b | 4 | 0.56 c | 4 | 0.25 d |
| 33.4 + 16.7 | | 4 | 6.3 b | 4 | 0.0 b | 4 | 308.4 a | 4 | 1.512 b | 4 | 0.63 c | 4 | 0.00 d |
| 40 + 20 | | 4 | 0.0 b | 4 | 0.0 b | 4 | 300.4 a | 4 | 1.409 b | 4 | 0.06 c | 4 | 0.00 d |
| 46.7 + 23.3 | | 4 | 0.0 b | 4 | 0.0 b | 4 | 303.7 a | 4 | 1.475 b | 4 | 0.00 c | 4 | 0.00 d |
| 53.4 + 26.6 | | 4 | 0.0 b | 4 | 0.0 b | 4 | 291.3 a | 4 | 1.505 b | 4 | 0.00 c | 4 | 0.00 d |
| 22.5 + 7.5 | | 4 | 0.0 b | 4 | 0.0 b | 4 | 294.8 a | 4 | 1.493 b | 4 | 3.44 c | 4 | 1.31 d |
| 30 + 10 | | 4 | 0.0 b | 4 | 0.0 b | 4 | 314.4 a | 4 | 1.385 b | 4 | 0.31 c | 4 | 0.06 d |
| 37.5 + 12.5 | | 4 | 0.0 b | 4 | 0.0 b | 4 | 293.2 a | 4 | 1.507 b | 4 | 0.13 c | 4 | 0.00 d |
| 45 + 15 | | 4 | 0.0 b | 4 | 0.0 b | 4 | 314.2 a | 4 | 1.479 b | 4 | 0.00 c | 4 | 0.00 d |
| 52.5 + 17.5 | | 4 | 0.0 b | 4 | 0.0 b | 4 | 302.3 a | 4 | 1.450 b | 4 | 0.06 c | 4 | 0.00 d |
| 60 + 20 | | 4 | 0.0 b | 4 | 0.0 b | 4 | 281.3 a | 4 | 1.522 b | 4 | 0.31 c | 4 | 0.00 d |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 19 | 129.5 | 19 | 125.0 | 19 | 3452.9 | 19 | 0.147 | 19 | 17.71 | 19 | 3.58 |
| Error | 60 | 28.6 | 60 | 20.8 | 60 | 467.7 | 60 | 0.019 | 60 | 0.43 | 60 | 0.11 |

TABLE 16

| Inoculated with E. tenella and E. maxima | | | | | | | | | | | | |
|---|---|---|---|---|---|---|---|---|---|---|---|---|
| | | | | | | | | | | Lesion Scores | | |
| Treatment | | Mortality | | Mean | | Wt. Gain | | Feed/Gain | | Intestinal | | Cecal |
| PPM | | # | Total % | # | % DTC | # | Mean | # | Mean | # | Mean | # | Mean |
| NC 0 | | 4 | 0.0 a | 4 | 0.0 a | 4 | 337.0 a | 4 | 1.396 b | 4 | 0.00 c | 4 | 0.00 d |
| IC 0 | | 4 | 0.0 a | 4 | 0.0 a | 4 | 245.3 c | 4 | 1.808 a | 4 | 8.00 a | 4 | 3.63 a |

Portmicin and Example 1

| | | | | | | | | | | | | |
|---|---|---|---|---|---|---|---|---|---|---|---|---|
| 15 + 15 | | 4 | 0.0 a | 4 | 0.0 a | 4 | 290.5 a-c | 4 | 1.535 a-b | 4 | 1.75 c | 4 | 2.81 a-b |
| 20 + 20 | | 4 | 0.0 a | 4 | 0.0 a | 4 | 300.4 a-c | 4 | 1.449 b | 4 | 0.75 c | 4 | 0.75 d |
| 25 + 25 | | 4 | 0.0 a | 4 | 0.0 a | 4 | 334.5 a | 4 | 1.370 b | 4 | 0.06 c | 4 | 0.44 d |
| 30 + 30 | | 4 | 0.0 a | 4 | 0.0 a | 4 | 318.6 a-b | 4 | 1.500 a-b | 4 | 0.00 c | 4 | 0.00 d |
| 35 + 35 | | 4 | 0.0 a | 4 | 0.0 a | 4 | 301.1 a-c | 4 | 1.516 a-b | 4 | 0.00 c | 4 | 0.13 d |
| 40 + 40 | | 4 | 0.0 a | 4 | 0.0 a | 4 | 298.6 a-c | 4 | 1.547 a-b | 4 | 0.00 c | 4 | 0.19 d |
| 20 + 10 | | 4 | 6.3 a | 4 | 6.3 a | 4 | 288.1 a-c | 4 | 1.560 a-b | 4 | 2.13 c | 4 | 2.88 a-b |
| 26.7 + 13.3 | | 4 | 6.3 a | 4 | 0.0 a | 4 | 302.9 a-c | 4 | 1.582 b | 4 | 1.50 c | 4 | 2.98 a |
| 33.4 + 16.7 | | 4 | 0.0 a | 4 | 0.0 a | 4 | 324.7 a-b | 4 | 1.448 b | 4 | 0.38 c | 4 | 0.38 d |
| 40 + 20 | | 4 | 0.0 a | 4 | 0.0 a | 4 | 331.2 a | 4 | 1.382 a-b | 4 | 0.00 c | 4 | 0.31 d |
| 46.7 + 23.3 | | 4 | 0.0 a | 4 | 0.0 a | 4 | 287.6 a-c | 4 | 1.572 a-b | 4 | 0.00 c | 4 | 0.19 d |
| 53.4 + 26.6 | | 4 | 0.0 a | 4 | 0.0 a | 4 | 265.8 b-c | 4 | 1.641 a-b | 4 | 0.00 c | 4 | 0.00 d |
| 22.5 + 7.5 | | 4 | 0.0 a | 4 | 0.0 a | 4 | 286.6 a-c | 4 | 1.548 a-b | 4 | 5.00 b | 4 | 3.63 a |
| 30 + 10 | | 4 | 0.0 a | 4 | 0.0 a | 4 | 300.3 a-c | 4 | 1.519 a-b | 4 | 2.50 c | 4 | 2.50 a-b |
| 37.5 + 12.5 | | 4 | 0.0 a | 4 | 0.0 a | 4 | 323.2 a-b | 4 | 1.436 b | 4 | 0.00 c | 4 | 1.81 b-c |
| 45 + 15 | | 4 | 0.0 a | 4 | 0.0 a | 4 | 297.6 a-c | 4 | 1.537 a-b | 4 | 0.13 c | 4 | 1.06 c-d |
| 52.5 + 17.5 | | 4 | 0.0 a | 4 | 0.0 a | 4 | 277.1 a-c | 4 | 1.587 a-b | 4 | 0.00 c | 4 | 0.13 d |
| 60 + 20 | | 4 | 6.3 a | 4 | 0.0 a | 4 | 276.2 a-c | 4 | 1.637 a-b | 4 | 0.00 c | 4 | 0.00 d |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 19 | 21.0 | 19 | 7.8 | 19 | 2284.6 | 19 | 0.042 | 19 | 17.09 | 19 | 7.32 |
| Error | 60 | 23.4 | 60 | 7.8 | 60 | 561.6 | 60 | 0.015 | 60 | 1.14 | 60 | 0.33 |

TABLE 17

Inoculated with *E. tenella*, *E. acervulina* and *E. maxima*

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 4 | 0.0 a | 4 | 0.0 a | 4 | 328.8 a | 4 | 1.455 a | 4 | 0.31 e | 4 | 0.00 d |
| IC 0 | 4 | 0.0 a | 4 | 0.0 a | 4 | 265.8 a | 4 | 1.715 a | 4 | 7.56 a | 4 | 3.50 a |
| Portmicin and Example 1 | | | | | | | | | | | | |
| 15 + 15 | 4 | 0.0 a | 4 | 0.0 a | 4 | 284.7 a | 4 | 1.610 b | 4 | 5.38 a–d | 4 | 2.25 d |
| 20 + 20 | 4 | 0.0 a | 4 | 0.0 a | 4 | 321.4 a | 4 | 1.523 b | 4 | 3.50 b–e | 4 | 1.25 c–e |
| 25 + 25 | 4 | 6.3 a | 4 | 0.0 a | 4 | 310.3 a | 4 | 1.682 b | 4 | 2.69 c–e | 4 | 0.48 d |
| 30 + 30 | 4 | 0.0 a | 4 | 0.0 a | 4 | 334.9 a | 4 | 1.438 b | 4 | 2.56 c–e | 4 | 0.13 d |
| 35 + 35 | 4 | 0.0 a | 4 | 0.0 a | 4 | 315.9 a | 4 | 1.557 b | 4 | 1.31 e | 4 | 0.13 d |
| 40 + 40 | 4 | 6.3 a | 4 | 0.0 a | 4 | 321.8 a | 4 | 1.558 b | 4 | 1.25 e | 4 | 0.19 d |
| 20 + 10 | 4 | 6.3 a | 4 | 0.0 a | 4 | 284.1 a | 4 | 1.667 b | 4 | 6.63 a–b | 4 | 2.83 a–b |
| 26.7 + 13.3 | 4 | 0.0 a | 4 | 0.0 a | 4 | 302.2 a | 4 | 1.589 b | 4 | 6.00 a–c | 4 | 2.44 a–b |
| 33.4 + 16.7 | 4 | 0.0 a | 4 | 0.0 a | 4 | 313.0 a | 4 | 1.543 b | 4 | 3.81 b–e | 4 | 0.75 d |
| 40 + 20 | 4 | 0.0 a | 4 | 0.0 a | 4 | 320.6 a | 4 | 1.486 b | 4 | 2.69 c–e | 4 | 0.19 d |
| 46.7 + 23.3 | 4 | 0.0 a | 4 | 0.0 a | 4 | 317.1 a | 4 | 1.450 b | 4 | 1.75 e | 4 | 0.31 d |
| 53.4 + 26.6 | 4 | 0.0 a | 4 | 0.0 a | 4 | 286.7 a | 4 | 1.553 b | 4 | 1.63 e | 4 | 0.13 d |
| 22.5 + 7.5 | 4 | 6.3 a | 4 | 0.0 a | 4 | 299.8 a | 4 | 1.667 b | 4 | 5.21 a–d | 4 | 2.50 a–b |
| 30 + 10 | 4 | 6.3 a | 4 | 0.0 a | 4 | 275.2 a | 4 | 1.695 b | 4 | 6.17 a–b | 4 | 2.54 a–b |
| 37.5 + 12.5 | 4 | 6.3 a | 4 | 0.0 a | 4 | 295.6 a | 4 | 1.656 b | 4 | 5.65 a–c | 4 | 1.73 b–c |
| 45 + 15 | 4 | 6.3 a | 4 | 0.0 a | 4 | 320.1 a | 4 | 1.517 b | 4 | 2.88 c–e | 4 | 0.65 d |
| 52.5 + 17.5 | 4 | 6.3 a | 4 | 0.0 a | 4 | 315.7 a | 4 | 1.592 b | 4 | 2.08 d–e | 4 | 0.25 d |
| 60 + 20 | 4 | 0.0 a | 4 | 0.0 a | 4 | 277.7 a | 4 | 1.772 b | 4 | 2.00 d–e | 4 | 0.13 d |
| Source of Variance | df | Mean Square | df | Mean Square | df | Mean Square | df | Mean Square | df | Mean Square | df | Mean Square |
| Treat. | 19 | 39.5 | 19 | 0.0 | 19 | 1563.8 | 19 | 0.036 | 19 | 17.71 | 19 | 5.28 |
| Error | 60 | 62.5 | 60 | 0.0 | 60 | 745.8 | 60 | 0.018 | 60 | 2.19 | 60 | 0.30 |

TABLE 18

Inoculated with *E. tenella* and *E. acervulina*
(No infected control in this experiment)

| Treatment | Mortality | | Mean | | Wt. Gain | | Feed/Gain | | Lesion Scores | | | |
|---|---|---|---|---|---|---|---|---|---|---|---|---|
| | | | | | | | | | Intestinal | | Cecal | |
| PPM | # | Total % | # | % DTC | # | Mean | # | Mean | # | Mean | # | Mean |
| NC 0 | 1 | 0.0 j | 1 | 0.0 j | 1 | 250.9 a | 1 | 1.361 j | 1 | 0.00 j | 1 | 0.00 j |
| Example 5 | | | | | | | | | | | | |
| 75 | 1 | 25.0 e | 1 | 25.0 d | 1 | 151.5 h | 1 | 1.811 d | 1 | 9.00 b | 1 | 3.50 b |
| Example 4 | | | | | | | | | | | | |
| 50 | 1 | 25.0 e | 1 | 25.0 d | 1 | 159.1 g | 1 | 1.905 c | 1 | 9.00 b | 1 | 3.50 b |
| 100 | 1 | 0.0 j | 1 | 0.0 j | 1 | 215.6 c | 1 | 1.480 h | 1 | 3.75 f | 2 | 2.00 f |
| Example 3 | | | | | | | | | | | | |
| 50 | 1 | 0.0 j | 1 | 0.0 j | 1 | 206.6 d | 1 | 1.502 g | 1 | 5.50 e | 1 | 2.50 e |
| 100 | 1 | 100.0 a | 1 | 25.0 d | 0 | 0.0 i | 1 | 9.980 a | 1 | 2.00 g | 1 | 0.00 j |
| Example 1 | | | | | | | | | | | | |
| 50 | 1 | 0.0 j | 1 | 0.0 j | 1 | 226.1 b | 1 | 1.446 i | 1 | 1.00 h | 1 | 1.50 g |
| 100 | 1 | 25.0 e | 1 | 0.0 j | 1 | 196.2 f | 1 | 1.805 e | 1 | 0.00 j | 1 | 0.67 h |
| Example 6 | | | | | | | | | | | | |
| 50 | 1 | 25.0 e | 1 | 25.0 d | 1 | 148.9 i | 1 | 1.905 c | 1 | 8.50 c | 1 | 3.25 c |
| 100 | 1 | 0.0 j | 1 | 0.0 j | 1 | 199.4 e | 1 | 1.577 f | 1 | 7.25 d | 1 | 2.50 e |

TABLE 18-continued

Inoculated with *E. tenella* and *E. acervulina*
(No infected control in this experiment)

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 9 | 944.4 | 9 | 166.7 | 9 | 8843.9 | 9 | 6.990 | 9 | 13.84 | 9 | 1.84 |
| Error | 0 | 0.0 | 0 | 0.0 | 0 | 0.0 | 0 | 0.000 | 0 | 0.00 | 0 | 0.00 |

TABLE 19

Inoculated with *E. tenella* and *E. acervulina*

| Treatment | Mortality | | Mean | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC 0 | 4 | 0.0 a | 4 | 0.0 a | 4 | 312.7 a | 4 | 1.334 d | 4 | 0.00 c | 4 | 0.00 e |
| IC 0 | 4 | 6.3 a | 4 | 6.3 a | 4 | 169.3 a | 4 | 2.146 a | 4 | 8.94 a | 4 | 3.44 a–b |
| Example 10 | | | | | | | | | | | | |
| 18 | 4 | 0.0 a | 4 | 0.0 a | 4 | 175.7 c | 4 | 1.920 b | 4 | 8.81 a | 4 | 3.63 a |
| 36 | 4 | 0.0 a | 4 | 0.0 a | 4 | 218.6 b | 4 | 1.691 c | 4 | 8.31 a | 4 | 2.50 c |
| 54 | 4 | 0.0 a | 4 | 0.0 a | 4 | 275.3 a | 4 | 1.481 d | 4 | 5.13 b | 4 | 1.56 d |
| 72 | 4 | 0.0 a | 4 | 0.0 a | 4 | 282.4 a | 4 | 1.417 d | 4 | 0.94 c | 4 | 0.50 e |
| Example 1 | | | | | | | | | | | | |
| 18 | 4 | 0.0 a | 4 | 0.0 a | 4 | 192.1 b–c | 4 | 1.837 b–c | 4 | 8.88 a | 4 | 2.69 b–c |
| 36 | 4 | 0.0 a | 4 | 0.0 a | 4 | 273.4 a | 4 | 1.396 d | 4 | 1.75 c | 4 | 0.81 d–e |
| 54 | 4 | 0.0 a | 4 | 0.0 a | 4 | 276.4 a | 4 | 1.357 d | 4 | 0.00 c | 4 | 0.44 e |
| 72 | 4 | 0.0 a | 4 | 0.0 a | 4 | 270.8 a | 4 | 1.458 d | 4 | 0.13 c | 4 | 0.13 e |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 9 | 15.6 | 9 | 15.6 | 9 | 10390.9 | 9 | 0.313 | 9 | 67.47 | 9 | 7.72 |
| Error | 30 | 15.6 | 30 | 15.6 | 30 | 416.2 | 30 | 0.014 | 30 | 1.28 | 30 | 0.27 |

TABLE 20

Inoculated with *E. tenella* and *E. acervulina*

| Treatment | Mortality | | Mean | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC 0 | 4 | 6.3 a | 4 | 0.0 a | 4 | 325.4 a | 4 | 1.444 c | 4 | 0.00 d | 4 | 0.00 d |
| IC 0 | 4 | 25.0 a | 4 | 25.0 a | 4 | 198.3 e | 4 | 2.022 a | 4 | 5.81 a–b | 4 | 3.81 a |
| Example 1 | | | | | | | | | | | | |
| 15 | 4 | 18.8 a | 4 | 12.5 a | 4 | 204.6 e | 4 | 1.909 a–b | 4 | 7.00 a | 4 | 4.00 a |
| 30 | 4 | 0.0 a | 4 | 0.0 a | 4 | 271.4 a–d | 4 | 1.529 c | 4 | 2.50 c | 4 | 2.44 b |
| 45 | 4 | 0.0 a | 4 | 0.0 a | 4 | 296.9 a–c | 4 | 1.466 c | 4 | 0.19 d | 4 | 0.31 d |
| Salinomycin | | | | | | | | | | | | |
| 22 | 4 | 12.5 a | 4 | 6.3 a | 4 | 241.1 c–e | 4 | 1.669 a–c | 4 | 4.58 b | 4 | 3.63 a |
| 44 | 4 | 12.5 a | 4 | 12.5 a | 4 | 248.9 b–e | 4 | 1.749 a–c | 4 | 3.25 c | 4 | 3.69 a |
| Salinomycin + Example 1 | | | | | | | | | | | | |
| 22 + 15 | 4 | 12.5 a | 4 | 12.5 a | 4 | 270.8 a–d | 4 | 1.700 a–c | 4 | 2.69 c | 4 | 3.56 a |
| 22 + 30 | 4 | 6.3 a | 4 | 0.0 a | 4 | 296.9 a–c | 4 | 1.490 c | 4 | 0.00 d | 4 | 1.23 c |
| 22 + 45 | 4 | 6.3 a | 4 | 0.0 a | 4 | 292.1 a–c | 4 | 1.473 c | 4 | 0.00 d | 4 | 0.08 d |
| Salinomycin + Example 1 | | | | | | | | | | | | |
| 44 + 15 | 4 | 0.0 a | 4 | 0.0 a | 4 | 312.0 a–b | 4 | 1.439 c | 4 | 0.13 d | 4 | 2.50 b |

TABLE 20-continued

Inoculated with *E. tenella* and *E. acervulina*

| | | | | | | | | | | | | | |
|---|---|---|---|---|---|---|---|---|---|---|---|---|---|
| 44 + 30 | | 4 | 6.3 a | 4 | 0.0 a | 4 | 318.3 a | 4 | 1.448 c | 4 | 0.00 d | 4 | 0.54 d |
| 44 + 45 | | 4 | 0.0 a | 4 | 0.0 a | 4 | 305.3 a–c | 4 | 1.404 c | 4 | 0.00 d | 4 | 0.25 d |
| Salinomycin | | | | | | | | | | | | | |
| 11 | | 4 | 12.5 a | 4 | 12.5 a | 4 | 218.4 d–e | 4 | 1.918 a–b | 4 | 6.63 a | 4 | 3.56 a |
| Salinomycin + Example 1 | | | | | | | | | | | | | |
| 11 + 15 | | 4 | 25.0 a | 4 | 25.0 a | 4 | 263.7 a–d | 4 | 1.688 a–c | 4 | 4.56 b | 4 | 3.94 a |
| 11 + 30 | | 4 | 6.3 a | 4 | 0.0 a | 4 | 287.2 a–c | 4 | 1.596 b–c | 4 | 0.38 d | 4 | 1.60 c |
| 11 + 45 | | 4 | 0.0 a | 4 | 0.0 a | 4 | 311.7 a–b | 4 | 1.522 c | 4 | 0.00 d | 4 | 0.00 d |
| Source of Variance | df | | Mean Square | df | Mean Square | df | Mean Square | df | Mean Square | df | Mean Square | df | Mean Square |
| Treat. | 16 | | 274.6 | 16 | 312.5 | 16 | 6369.2 | 16 | 0.146 | 16 | 27.27 | 16 | 10.56 |
| Error | 51 | | 226.7 | 51 | 156.3 | 51 | 794.6 | 51 | 0.028 | 51 | 0.59 | 51 | 0.13 |

TABLE 21

Inoculated with *E. tenella* and *E. acervulina*

| Treatment | Mortality | | Mean | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC 0 | 2 | 0.0 b | 2 | 0.0 a | 2 | 300.6 a | 2 | 1.371 d | 2 | 0.00 c | 2 | 0.00 c |
| IC 0 | 2 | 12.5 b | 2 | 12.5 a | 2 | 165.7 b–c | 2 | 1.974 b | 2 | 6.13 a | 2 | 3.63 a |
| Example 1 | | | | | | | | | | | | |
| 12.5 | 2 | 25.0 b | 2 | 12.5 a | 2 | 210.7 a–b | 2 | 1.740 c | 2 | 4.21 b | 2 | 4.00 a |
| 25 | 2 | 0.0 b | 2 | 0.0 a | 2 | 275.6 a | 2 | 1.374 d | 2 | 0.25 c | 2 | 2.25 b |
| 50 | 2 | 0.0 b | 2 | 0.0 a | 2 | 291.2 a | 2 | 1.381 d | 2 | 0.00 c | 2 | 0.63 c |
| 100 | 1 | 50.0 a | 1 | 0.0 a | 1 | 115.8 c | 1 | 3.416 a | 1 | 0.00 c | 1 | 0.00 c |
| Example 18 | | | | | | | | | | | | |
| 12.5 | 2 | 12.5 b | 2 | 12.5 a | 2 | 219.4 a–b | 2 | 1.598 c–d | 2 | 5.75 a | 2 | 3.75 a |
| 25 | 2 | 0.0 b | 2 | 0.0 a | 2 | 292.4 a | 2 | 1.361 d | 2 | 0.13 c | 2 | 0.75 c |
| 50 | 2 | 0.0 b | 2 | 0.0 a | 2 | 242.9 a–b | 2 | 1.526 c–d | 2 | 0.00 c | 2 | 0.00 c |
| Source of Variance | df | Mean Square | df | Mean Square | df | Mean Square | df | Mean Square | df | Mean Square | df | Mean Square |
| Treat. | 8 | 381.4 | 8 | 75.8 | 8 | 6198.6 | 8 | 0.500 | 8 | 14.12 | 8 | 5.69 |
| Error | 8 | 78.1 | 8 | 117.2 | 8 | 636.4 | 8 | 0.007 | 8 | 0.11 | 8 | 0.15 |

TABLE 22

Inoculated with *E. tenella*, *E. acervulina* and *E. maxima*

| Treatment | Mortality | | Mean | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC 0 | 4 | 0.0 h | 4 | 0.0 h | 4 | 305.7 a | 4 | 1.374 h | 4 | 0.00 k | 4 | 0.00 e |
| IC 0 | 4 | 0.0 h | 4 | 0.0 h | 4 | 247.0 e–h | 4 | 1.549 a–f | 4 | 7.50 a–c | 4 | 2.50 a–b |
| Example 1 | | | | | | | | | | | | |
| 15 | 4 | 0.0 h | 4 | 0.0 h | 4 | 256.2 b–h | 4 | 1.525 a–h | 4 | 8.81 a | 4 | 1.88 b–c |
| 30 | 4 | 0.0 h | 4 | 0.0 h | 4 | 266.3 a–h | 4 | 1.489 a–h | 4 | 5.63 c–f | 4 | 0.13 e |
| 45 | 4 | 0.0 h | 4 | 0.0 h | 4 | 278.2 a–h | 4 | 1.427 b–h | 4 | 3.81 d–i | 4 | 0.00 e |
| Portmicin | | | | | | | | | | | | |
| 15 | 4 | 6.3 a–h | 4 | 0.0 h | 4 | 241.8 g–h | 4 | 1.685 a | 4 | 8.69 a | 4 | 3.56 a |
| 30 | 4 | 0.0 h | 4 | 0.0 h | 4 | 269.0 a–h | 4 | 1.488 a–h | 4 | 6.31 b–d | 4 | 2.69 a–b |

TABLE 22-continued

Inoculated with E. tenella, E. acervulina and E. maxima

| | | | | | | | | | | | |
|---|---|---|---|---|---|---|---|---|---|---|---|
| 45 | 4 | 0.0 h | 4 | 0.0 h | 4 | 258.6 a–h | 4 | 1.561 a–e | 4 | 7.63 a–c | 4 | 1.75 b–d |
| Salinomycin | | | | | | | | | | | |
| 15 | 4 | 6.3 a–h | 4 | 0.0 h | 4 | 245.4 f–h | 4 | 1.603 a–c | 4 | 8.17 a–b | 4 | 3.06 a |
| 30 | 4 | 0.0 h | 4 | 0.0 h | 4 | 239.3 h | 4 | 1.638 a–b | 4 | 8.25 a–b | 4 | 3.56 a |
| 45 | 4 | 0.0 h | 4 | 0.0 h | 4 | 255.8 c–h | 4 | 1.562 a–e | 4 | 6.31 b–d | 4 | 2.88 a–b |
| Portmicin + Example 1 | | | | | | | | | | | |
| 15 + 15 | 4 | 6.3 a–h | 4 | 0.0 h | 4 | 277.0 a–h | 4 | 1.492 a–h | 4 | 5.00 d–g | 4 | 0.69 d–e |
| 15 + 30 | 4 | 0.0 h | 4 | 0.0 h | 4 | 262.3 a–h | 4 | 1.528 a–h | 4 | 3.44 e–j | 4 | 0.00 e |
| 15 + 45 | 4 | 6.3 a–h | 4 | 6.3 a | 4 | 251.4 d–h | 4 | 1.544 a–g | 4 | 2.50 g–j | 4 | 0.06 e |
| 30 + 15 | 4 | 0.0 h | 4 | 0.0 h | 4 | 275.0 a–h | 4 | 1.447 a–h | 4 | 4.06 d–h | 4 | 0.03 e |
| 30 + 30 | 4 | 6.3 a–h | 4 | 0.0 h | 4 | 268.8 a–h | 4 | 1.454 a–h | 4 | 1.75 h–k | 4 | 0.00 e |
| 30 + 45 | 4 | 6.3 a–h | 4 | 0.0 h | 4 | 283.6 a–e | 4 | 1.430 a–h | 4 | 1.15 j–k | 4 | 0.00 e |
| 45 + 15 | 4 | 0.0 h | 4 | 0.0 h | 4 | 282.4 a–f | 4 | 1.401 f–h | 4 | 2.81 g–j | 4 | 0.00 e |
| 45 + 30 | 4 | 0.0 h | 4 | 0.0 h | 4 | 276.9 a–h | 4 | 1.420 e–h | 4 | 1.69 h–k | 4 | 0.00 e |
| 45 + 45 | 4 | 0.0 h | 4 | 0.0 h | 4 | 278.1 a–h | 4 | 1.429 a–h | 4 | 1.13 j–k | 4 | 0.00 e |
| Salinomycin + Example 1 | | | | | | | | | | | |
| 15 + 15 | 4 | 0.0 h | 4 | 0.0 h | 4 | 277.3 a–h | 4 | 1.440 a–h | 4 | 5.81 c–e | 4 | 1.75 b–d |
| 15 + 30 | 4 | 0.0 h | 4 | 0.0 h | 4 | 292.8 a–c | 4 | 1.394 g–h | 4 | 4.44 d–g | 4 | 0.31 e |
| 15 + 45 | 4 | 0.0 h | 4 | 0.0 h | 4 | 274.0 a–h | 4 | 1.423 d–h | 4 | 3.31 e–j | 4 | 0.00 e |
| 30 + 15 | 4 | 0.0 h | 4 | 0.0 h | 4 | 282.2 a–g | 4 | 1.528 a–h | 4 | 4.75 d–g | 4 | 1.00 c–e |
| 30 + 30 | 4 | 0.0 h | 4 | 0.0 h | 4 | 269.6 a–h | 4 | 1.453 a–h | 4 | 3.13 f–j | 4 | 0.00 e |
| 30 + 45 | 4 | 0.0 h | 4 | 0.0 h | 4 | 276.0 a–h | 4 | 1.435 a–h | 4 | 1.06 j–k | 4 | 0.38 e |
| 45 + 15 | 4 | 6.3 a–h | 4 | 0.0 h | 4 | 294.3 a–b | 4 | 1.425 c–h | 4 | 4.15 d–h | 4 | 0.71 d–e |
| 45 + 30 | 4 | 0.0 h | 4 | 0.0 h | 4 | 264.0 a–h | 4 | 1.438 a–h | 4 | 1.50 i–k | 4 | 0.06 e |
| 45 + 45 | 4 | 12.5 a | 4 | 0.0 h | 4 | 285.8 a–d | 4 | 1.441 a–h | 4 | 0.83 j–k | 4 | 0.00 e |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 28 | 45.8 | 28 | 5.4 | 28 | 1048.4 | 28 | 0.023 | 28 | 27.90 | 28 | 6.17 |
| Error | 87 | 44.9 | 87 | 5.4 | 87 | 350.9 | 87 | 0.009 | 87 | 1.20 | 87 | 0.30 |

TABLE 23

Inoculated with E. tenella, E. acervulina and E. maxima

| Treatment | Mortality | | Mean | | Wt. Gain | | Feed/Gain | | Lesion Scores Intestinal | | Cecal | |
|---|---|---|---|---|---|---|---|---|---|---|---|---|
| PPM | # | Total % | # | % DTC | # | Mean | # | Mean | # | Mean | # | Mean |
| NC 0 | 4 | 0.0 h | 4 | 0.0 a | 4 | 311.1 a | 4 | 1.331 b–g | 4 | 0.00 i | 4 | 0.00 c |
| IC 0 | 4 | 0.0 h | 4 | 0.0 a | 4 | 240.6 f–h | 4 | 1.538 b–e | 4 | 9.44 a | 4 | 2.88 a–b |
| Example 1 | | | | | | | | | | | | |
| 15 | 4 | 0.0 h | 4 | 0.0 a | 4 | 250.2 c–g | 4 | 1.561 b | 4 | 8.88 a–b | 4 | 3.19 a |
| 30 | 4 | 0.0 h | 4 | 0.0 a | 4 | 271.8 a–g | 4 | 1.412 b–g | 4 | 6.63 c–d | 4 | 0.31 c |
| 45 | 4 | 0.0 h | 4 | 0.0 a | 4 | 257.4 b–g | 4 | 1.540 b–d | 4 | 3.31 f–h | 4 | 0.31 c |
| Portmicin | | | | | | | | | | | | |
| 15 | 4 | 0.0 h | 4 | 0.0 a | 4 | 207.6 h | 4 | 1.912 a | 4 | 9.38 a | 4 | 3.50 a |
| 30 | 4 | 0.0 h | 4 | 0.0 a | 4 | 252.9 b–g | 4 | 1.522 b–g | 4 | 8.00 a–c | 4 | 2.44 a–b |
| 45 | 4 | 0.0 h | 4 | 0.0 a | 4 | 244.1 e–h | 4 | 1.539 b–e | 4 | 7.06 b–d | 4 | 1.13 c |
| Salinomycin | | | | | | | | | | | | |
| 15 | 4 | 6.3 a–d | 4 | 0.0 a | 4 | 228.6 g–h | 4 | 1.837 a | 4 | 8.92 a–b | 4 | 3.10 a |
| 30 | 4 | 0.0 h | 4 | 0.0 a | 4 | 255.9 b–g | 4 | 1.522 b–g | 4 | 8.44 a–c | 4 | 3.38 a |
| 45 | 4 | 0.0 h | 4 | 0.0 a | 4 | 245.4 d–h | 4 | 1.526 b–f | 4 | 8.06 a–c | 4 | 2.50 a–b |
| Portmicin + Example 1 | | | | | | | | | | | | |
| 15 + 15 | 4 | 0.0 h | 4 | 0.0 a | 4 | 286.9 a–f | 4 | 1.410 b–g | 4 | 4.63 e–f | 4 | 0.38 c |
| 15 + 30 | 4 | 0.0 h | 4 | 0.0 a | 4 | 304.8 a–b | 4 | 1.320 e–g | 4 | 2.88 f–h | 4 | 0.00 c |
| 15 + 45 | 4 | 6.3 a–d | 4 | 6.3 a | 4 | 279.1 a–f | 4 | 1.444 b–g | 4 | 1.19 h–i | 4 | 0.00 c |
| 30 + 15 | 4 | 0.0 h | 4 | 0.0 a | 4 | 276.3 a–g | 4 | 1.389 b–g | 4 | 2.44 g–h | 4 | 0.00 c |
| 30 + 30 | 4 | 0.0 h | 4 | 0.0 a | 4 | 292.2 a–c | 4 | 1.339 b–g | 4 | 2.13 h–i | 4 | 0.06 c |
| 30 + 45 | 4 | 0.0 h | 4 | 0.0 a | 4 | 298.9 a–c | 4 | 1.320 e–g | 4 | 1.56 h–i | 4 | 0.00 c |
| 45 + 15 | 4 | 6.3 a–d | 4 | 0.0 a | 4 | 271.0 a–g | 4 | 1.419 b–g | 4 | 2.35 g–h | 4 | 0.00 c |
| 45 + 30 | 4 | 0.0 h | 4 | 0.0 a | 4 | 293.5 a–e | 4 | 1.387 b–g | 4 | 1.81 h–i | 4 | 0.19 c |
| 45 + 45 | 4 | 0.0 h | 4 | 0.0 a | 4 | 283.1 a–f | 4 | 1.326 c–g | 4 | 1.56 h–i | 4 | 0.00 c |

TABLE 23-continued

Inoculated with *E. tenella*, *E. acervulina* and *E. maxima*

Salinomycin + Example 1

| | | | | | | | | | | | | |
|---|---|---|---|---|---|---|---|---|---|---|---|---|
| 15 + 15 | | 4 | 0.0 h | 4 | 0.0 a | 4 | 264.5 a–g | 4 | 1.490 b–g | 4 | 5.81 d–e | 4 | 2.06 b |
| 15 + 30 | | 4 | 0.0 h | 4 | 0.0 a | 4 | 288.0 a–f | 4 | 1.380 b–g | 4 | 4.69 e–f | 4 | 0.88 c |
| 15 + 45 | | 4 | 0.0 h | 4 | 0.0 a | 4 | 301.8 a–c | 4 | 1.338 b–g | 4 | 2.06 h–i | 4 | 0.00 c |
| 30 + 15 | | 4 | 0.0 h | 4 | 0.0 a | 4 | 289.5 a–f | 4 | 1.382 b–g | 4 | 4.44 e–g | 4 | 1.88 b |
| 30 + 30 | | 4 | 0.0 h | 4 | 0.0 a | 4 | 276.6 a–g | 4 | 1.470 b–g | 4 | 3.13 f–h | 4 | 0.25 c |
| 30 + 45 | | 4 | 6.3 a–d | 4 | 0.0 a | 4 | 291.3 a–f | 4 | 1.391 b–g | 4 | 1.00 h–i | 4 | 0.00 c |
| 45 + 15 | | 4 | 0.0 h | 4 | 0.0 a | 4 | 305.9 a–b | 4 | 1.295 g | 4 | 3.13 f–h | 4 | 0.75 c |
| 45 + 30 | | 4 | 0.0 h | 4 | 0.0 a | 4 | 297.6 a–d | 4 | 1.306 f–g | 4 | 2.06 h–i | 4 | 0.06 c |
| 45 + 45 | | 4 | 0.0 h | 4 | 0.0 a | 4 | 281.4 a–f | 4 | 1.413 b–g | 4 | 1.00 h–i | 4 | 0.19 c |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 28 | 19.2 | 28 | 0.0 | 28 | 2628.9 | 28 | 0.082 | 28 | 36.26 | 28 | 6.41 |
| Error | 87 | 21.6 | 87 | 0.0 | 87 | 407.7 | 87 | 0.013 | 87 | 0.98 | 87 | 0.26 |

TABLE 24

Inoculated with *E. tenella*, *E. acervulina* and *E. maxima*

| | Mortality | | Mean | | Wt. Gain | | Feed/Gain | | Lesion Scores | |
|---|---|---|---|---|---|---|---|---|---|---|
| | | | | | | | | | Intestinal | Cecal |
| Treatment PPM | # | Total % | # | % DTC | # | Mean | # | Mean | # Mean | # Mean |
| NC 0 | 4 | 0.0 h | 4 | 0.0 h | 4 | 333.2 a | 4 | 1.304 g–h | 4 0.00 k | 4 0.00 e |
| IC 0 | 4 | 0.0 h | 4 | 0.0 h | 4 | 270.6 f–h | 4 | 1.469 a–b | 4 7.88 a | 4 2.56 a–b |
| Example 18 | | | | | | | | | | |
| 15 | 4 | 0.0 h | 4 | 0.0 h | 4 | 277.5 d–h | 4 | 1.426 a–h | 4 7.94 a | 4 1.50 c |
| 30 | 4 | 6.3 a–dh | 4 | 0.0 h | 4 | 303.4 a–h | 4 | 1.347 a–h | 4 4.63 b–d | 4 0.00 e |
| 45 | 4 | 0.0 h | 4 | 0.0 h | 4 | 298.7 a–h | 4 | 1.317 d–h | 4 2.56 e–i | 4 0.00 e |
| Example 1 | | | | | | | | | | |
| 15 | 4 | 6.3 a–d | 4 | 6.3 a | 4 | 280.1 b–h | 4 | 1.436 a–g | 4 7.13 a | 4 2.06 b |
| 30 | 4 | 0.0 h | 4 | 0.0 h | 4 | 294.3 a–h | 4 | 1.392 a–h | 4 7.00 a | 4 0.13 d–e |
| 45 | 4 | 0.0 h | 4 | 0.0 h | 4 | 300.9 a–h | 4 | 1.327 b–h | 4 3.69 c–f | 4 0.00 e |
| Portmicin | | | | | | | | | | |
| 15 | 4 | 0.0 h | 4 | 0.0 h | 4 | 277.8 c–h | 4 | 1.462 a–c | 4 8.06 a | 4 2.44 a–b |
| 30 | 4 | 0.0 h | 4 | 0.0 h | 4 | 264.8 h | 4 | 1.485 a | 4 7.94 a | 4 2.94 a |
| Portmicin + Example 18 | | | | | | | | | | |
| 15 + 15 | 4 | 0.0 h | 4 | 0.0 h | 4 | 305.0 a–h | 4 | 1.377 a–h | 4 4.69 b–d | 4 0.38 d–e |
| 15 + 30 | 4 | 0.0 h | 4 | 0.0 h | 4 | 311.1 a–e | 4 | 1.340 a–h | 4 3.25 d–g | 4 0.00 e |
| 15 + 45 | 4 | 0.0 h | 4 | 0.0 h | 4 | 307.9 a–f | 4 | 1.349 a–h | 4 1.56 g–k | 4 0.00 e |
| 30 + 15 | 4 | 0.0 h | 4 | 0.0 h | 4 | 301.9 a–h | 4 | 1.333 a–h | 4 3.94 b–e | 4 0.25 d–e |
| 30 + 30 | 4 | 0.0 h | 4 | 0.0 h | 4 | 298.3 a–h | 4 | 1.384 a–h | 4 1.50 g–k | 4 0.06 d–e |
| 30 + 45 | 4 | 0.0 h | 4 | 0.0 h | 4 | 289.6 a–h | 4 | 1.394 a–g | 4 0.88 h–k | 4 0.00 e |
| 45 + 15 | 4 | 6.3 a–d | 4 | 0.0 h | 4 | 313.9 a–d | 4 | 1.312 e–h | 4 2.25 e–j | 4 0.00 e |
| 45 + 30 | 4 | 0.0 h | 4 | 0.0 h | 4 | 304.5 a–h | 4 | 1.306 f–h | 4 1.13 g–k | 4 0.00 e |
| 45 + 45 | 4 | 0.0 h | 4 | 0.0 h | 4 | 265.7 g–h | 4 | 1.450 a–d | 4 0.19 j–k | 4 0.00 e |
| Portimicin + Example 1 | | | | | | | | | | |
| 15 + 15 | 4 | 6.3 a–h | 4 | 0.0 h | 4 | 316.2 a–b | 4 | 1.296 h | 4 5.31 b–c | 4 0.50 d |
| 15 + 30 | 4 | 0.0 h | 4 | 0.0 h | 4 | 305.9 a–h | 4 | 1.332 a–h | 4 2.94 d–h | 4 0.00 e |
| 15 + 45 | 4 | 0.0 h | 4 | 0.0 h | 4 | 285.4 a–h | 4 | 1.343 a–h | 4 1.94 e–k | 4 0.00 e |
| 30 + 15 | 4 | 0.0 h | 4 | 0.0 h | 4 | 306.5 a–g | 4 | 1.317 d–h | 4 3.00 d–h | 4 0.00 e |
| 30 + 30 | 4 | 0.0 h | 4 | 0.0 h | 4 | 305.8 a–h | 4 | 1.323 b–h | 4 1.81 f–k | 4 0.13 d–e |
| 30 + 45 | 4 | 0.0 h | 4 | 0.0 h | 4 | 304.7 a–h | 4 | 1.365 a–h | 4 1.56 g–k | 4 0.00 e |
| 45 + 15 | 4 | 0.0 h | 4 | 0.0 h | 4 | 315.4 a–c | 4 | 1.329 a–h | 4 2.63 e–i | 4 0.00 e |
| 45 + 30 | 4 | 0.0 h | 4 | 0.0 h | 4 | 279.5 b–h | 4 | 1.439 a–e | 4 1.44 g–k | 4 0.00 e |
| 45 + 45 | 4 | 0.0 h | 4 | 0.0 h | 4 | 280.7 b–h | 4 | 1.399 a–h | 4 0.69 i–k | 4 0.00 e |

| Source of Variance | df | Mean Square | df | Mean Square | df | Mean Square | df | Mean Square | df | Mean Square | df | Mean Square |
|---|---|---|---|---|---|---|---|---|---|---|---|---|
| Treat. | 28 | 19.2 | 28 | 5.4 | 28 | 1145.8 | 28 | 0.013 | 28 | 26.27 | 28 | 3.25 |
| Error | 87 | 21.6 | 87 | 5.4 | 87 | 383.7 | 87 | 0.004 | 87 | 0.77 | 87 | 0.10 |

A further trial was conducted, as described above, except that only one cage was used per treatment, and only weight gain, mortality, and lesion scores were recorded. The data were not evaluated statistically. Results are set forth in Table 25.

TABLE 25

| Treatment PPM | Inoculated with E. acervulina and E. tenella | | | | |
|---|---|---|---|---|---|
| | Final wt. (gms) | Wt. Gain | % Total Mortality | Lesion Scores Intestinal | Cecal |
| NC 0 | 370.2 | 231.0 | 0 | 0.00 | 0.00 |
| IC 0 | 264.6 | 126.8 | 0 | 8.75 | 3.50 |
| Example 14 | | | | | |
| 25 | 240.1 | 96.1 | 50 | 8.33 | 3.67 |
| 50 | 320.3 | 179.5 | 50 | 9.00 | 3.67 |
| 100 | 263.4 | 125.7 | 25 | 0.00 | 1.33 |
| Example 15 | | | | | |
| 25 | 255.9 | 113.8 | 50 | 9.00 | 2.50 |
| 50 | 310.8 | 173.1 | 0 | 2.75 | 2.75 |
| 100 | 278.6 | 140.9 | 0 | 0.00 | 0.00 |
| Example 16 | | | | | |
| 25 | 275.3 | 137.4 | 50 | 9.33 | 3.67 |
| 50 | 338.3 | 196.7 | 25 | 0.33 | 2.33 |
| 100 | 324.0 | 181.9 | 0 | 0.00 | 1.00 |
| Example 17 | | | | | |
| 25 | 316.7 | 176.3 | 0 | 3.00 | 4.00 |
| 50 | 313.3 | 175.2 | 25 | 0.00 | 1.00 |
| 100 | 137.3 | −2.8 | 75 | 0.00 | 3.00 |
| Example 11 | | | | | |
| 25 | 257.4 | 119.9 | 0 | 9.00 | 3.50 |
| 50 | 0.0 | 0.0 | 100 | 9.00 | 4.00 |
| 100 | 339.2 | 200.1 | 25 | 0.00 | 2.67 |
| Example 12 | | | | | |
| 25 | 215.4 | 76.7 | 25 | 9.00 | 3.67 |
| 50 | 136.2 | −2.7 | 75 | 9.00 | 3.67 |
| 100 | 287.6 | 147.0 | 75 | 9.00 | 4.00 |
| Example 13 | | | | | |
| 25 | 168.9 | 28.4 | 75 | 7.50 | 4.00 |
| 50 | 260.3 | 118.5 | 25 | 7.25 | 3.25 |
| 100 | 234.2 | 95.0 | 25 | 9.00 | 3.67 |
| Example 9 | | | | | |
| 25 | 270.9 | 130.2 | 0 | 7.25 | 2.50 |
| 50 | 315.7 | 176.7 | 0 | 0.00 | 2.00 |
| 100 | 270.0 | 129.6 | 0 | 0.00 | 0.00 |

A further trial was conducted, as described above, except that only one cage was used per treatment; only lesion scores were recorded; no control was employed; and the data were not evaluated statistically. Results are set forth in Table 26. No mortality occurred.

TABLE 26

| Treatment PPM | Inoculated with E. acervulina and E. tenella | |
|---|---|---|
| Example 20 | Lesion Scores | |
| | Intestinal | Cecal |
| 50 | | |
| bird #1 | 2 | 4 |
| bird #2 | 3 | 2 |
| bird #3 | 1 | 3 |

TABLE 26-continued

| Treatment PPM | Inoculated with E. acervulina and E. tenella | |
|---|---|---|
| Example 20 | Lesion Scores | |
| | Intestinal | Cecal |
| bird #4 | 2 | 4 |
| 100 | | |
| bird #1 | 3 | 4 |
| bird #2 | 3 | 4 |
| bird #3 | 3 | 4 |
| bird #4 | 2 | 4 |

I claim:

1. A compound of the formula

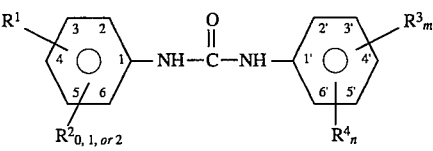

wherein $R^1$ represents perfluoroalkylsulfonyloxy of $C_1$–$C_8$ or 1,1,2,2-tetrafluoroethylsulfonyloxy, with the limitation that if no $R^2$ is present, $R^1$ is located at the 4-position;

$R^3$ represents perfluoroalkylsulfonyloxy of $C_1$–$C_8$ or 1,1,2,2-tetrafluoroethylsulfonyloxy, with the limitation that if no $R^4$ is present, $R^3$ is located at the 4'-position;

each $R^2$ and $R^4$ independently represents nitro, halo, cyano, thiocyanato, trifluoroacetylthio, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;

m represents 0 or 1;

n represents 0, 1, or 2; and the sum of m and n is 1, 2, or 3.

2. The compound of claim 1 wherein $R^1$ is $CF_3SO_2O$—.

3. The compound of claim 2 which is 4'-(trifluoromethylthio)-4-(trifluoromethylsulfonyloxy)carbanilide.

4. The compound of claim 2 which is 4'-(trifluoromethylsulfonyl)-4-(trifluoromethylsulfonyloxy)carbanilide.

5. A method of preventing or treating coccidiosis in a warm-blooded animal which comprises administering to the animal an effective amount of an active agent which is a compound of claim 1.

6. The method of claim 5 employing an active agent wherein $R^1$ is $CF_3SO_2O$—.

7. The method of claim 6 wherein the active agent is 4'-(trifluoromethylthio)-4-(trifluoromethylsulfonyloxy) carbanilide.

8. The method of claim 6 wherein the active agent is 4'-(trifluoromethylsulfonyl)-4-(trifluoromethylsulfonyloxy) carbanilide.

9. The method of claim 5 for the prevention or treatment of coccidiosis attributable to a polyether-resistant strain of protozoa.

10. The method of claim 9 employing an active agent wherein $R^1$ is $CF_3SO_2O$—.

11. The method of claim 10 wherein the active agent is 4'-(trifluoromethylthio)-4-(trifluoromethylsulfonyloxy) carbanilide.

12. The method of claim 10 wherein the active agent is 4'-(trifluoromethylsulfonyl)-4-(trifluoromethylsulfonyloxy)carbanilide.

13. An animal feed premix comprising from 0.1 to 50.0 percent by weight of an active agent which is a compound of claim 1.

14. The animal feed premix of claim 13 comprising an active agent wherein $R^1$ is $CF_3SO_2O$—.

15. The animal feed premix of claim 14 wherein the active agent is 4'-(trifluoromethylthio)-4-(trifluoromethylsulfonyloxy)carbanilide.

16. The animal feed premix of claim 14 wherein the active agent is 4'-(trifluoromethylsulfonyl)-4-(trifluoromethylsulfonyloxy)carbanilide.

17. An animal feed comprising from 0.001 to 0.02 percent by weight of an active agent which is a compound of claim 1.

18. The animal feed of claim 17 comprising an active agent wherein $R^1$ is $CF_3SO_2O$—.

19. The animal feed of claim 18 wherein the active agent is 4'-(trifluoromethylthio)-4-(trifluoromethylsulfonyloxy)carbanilide.

20. The animal feed of claim 18 wherein the active agent is 4'-(trifluoromethylsulfonyl)-4-(trifluoromethylsulfonyloxy)carbanilide.

21. A method of preventing or treating coccidiosis in a warm-blooded animal which comprises administering both a polyether antibiotic and a carbanilide compound of the formula

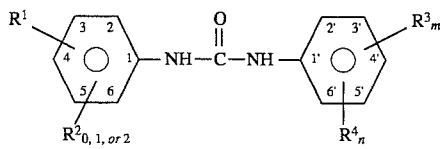

wherein
- $R^1$ represents perfluoroalkylsulfonyloxy of $C_1$–$C_8$ or 1,1,2,2-tetrafluoroethylsulfonyloxy, with the limitation that if no $R^2$ is present, $R^1$ is located at the 4-position;
- $R^3$ represents perfluoroalkylsulfonyloxy of $C_1$–$C_8$ or 1,1,2,2-tetrafluoroethylsulfonyloxy, with the limitation that if no $R^4$ is present, $R^3$ is located at the 4'-position;
- each $R^2$ and $R^4$ independently represents nitro, halo, cyano, thiocyanato, trifluoroacetylthio, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;
- m represents 0 or 1;
- n represents 0, 1, or 2; and
- the sum of m and n is 1, 2, or 3; in amounts which have a combined effect of preventing or treating coccidiosis.

22. The method of claim 21 wherein the polyether antibiotic is selected from the group consisting of
monensin,
narasin,
salinomycin,
laidlomycin,
portmicin, and A82810.

23. The method of claim 22 wherein the carbanilide compound is 4'-(trifluoromethylthio)-4-(trifluoromethylsulfonyloxy)carbanilide.

24. The method of claim 23 wherein the polyether antibiotic is monensin.

25. The method of claim 23 wherein the polyether antibiotic is narasin.

26. The method of claim 23 wherein the polyether antibiotic is salinomycin.

27. The method of claim 23 wherein the polyether antibiotic is laidlomycin.

28. The method of claim 23 wherein the polyether antibiotic is portmicin.

29. The method of claim 23 wherein the polyether antibiotic is A82810.

30. The method of claim 22 wherein the carbanilide compound is 4'-(trifluoromethylsulfonyl)-4-(trifluoromethylsulfonyloxy)carbanilide.

31. The method of claim 30 wherein the polyether antibiotic is monensin.

32. The method of claim 30 wherein the polyether antibiotic is narasin.

33. The method of claim 30 wherein the polyether antibiotic is salinomycin.

34. The method of claim 30 wherein the polyether antibiotic is laidlomycin.

35. The method of claim 30 wherein the polyether antibiotic is portmicin.

36. The method of claim 30 wherein the polyether antibiotic is A82810.

37. The method of claim 21 for the prevention or treatment of coccidiosis attributable to a polyether-resistant strain of protozoa.

38. The method of claim 37 wherein the polyether antibiotic is selected from the group consisting of
monensin,
narasin,
salinomycin,
laidlomycin,
portmicin, and A82810.

39. The method of claim 38 wherein the carbanilide compound is 4'-(trifluoromethylthio)-4-(trifluoromethylsulfonyloxy)carbanilide.

40. The method of claim 38 wherein the carbanilide compound is 4'-(trifluoromethylsulfonyl)-4-(trifluoromethylsulfonyloxy)carbanilide.

41. An animal feed premix useful for preventing or treating coccidiosis in a warm-blooded animal which comprises both a polyether antibiotic and a carbanilide compound of the formula

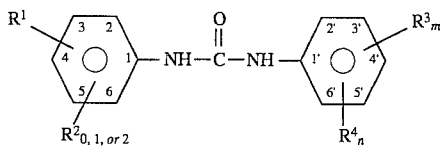

wherein
- $R^1$ represents perfluoroalkylsulfonyloxy of $C_1$–$C_8$ or 1,1,2,2-tetrafluoroethylsulfonyloxy, with the limitation that if no $R^2$ is present, $R^1$ is located at the 4-position;
- $R^3$ represents perfluoroalkylsulfonyloxy of $C_1$–$C_8$ or 1,1,2,2-tetrafluoroethylsulfonyloxy, with the limitation that if no $R^4$ is present, $R^3$ is located at the 4'-position;
- each $R^2$ and $R^4$ independently represents nitro, halo, cyano, thiocyanato, trifluoroacetylthio, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;

m represents 0 or 1;

n represents 0, 1, or 2; and the sum of m and n is 1, 2, or 3, each of said polyether antibiotic and said carbanilide compound being present in a concentration of from 0.2 to 25.0 percent by weight.

42. The animal feed premix of claim 41 wherein the polyether antibiotic is selected from the group consisting of monensin, narasin, salinomycin, laidlomycin, portmicin, and A82810.

43. The animal feed premix of claim 42 wherein the carbanilide compound is 4'-(trifluoromethylthio)-4-(trifluoromethylsulfonyloxy)carbanilide.

44. The animal feed premix of claim 43 wherein the polyether antibiotic is monensin.

45. The animal feed premix of claim 43 wherein the polyether antibiotic is narasin.

46. The animal feed premix of claim 43 wherein the polyether antibiotic is salinomycin.

47. The animal feed premix of claim 43 wherein the polyether antibiotic is laidlomycin.

48. The animal feed premix of claim 43 wherein the polyether antibiotic is portmicin.

49. The animal feed premix of claim 43 wherein the polyether antibiotic is A82810.

50. The animal feed premix of claim 42 wherein the carbanilide compound is 4'-(trifluoromethylsulfonyl)-4-(trifluoromethylsulfonyloxy)carbanilide.

51. The animal feed premix of claim 50 wherein the polyether antibiotic is monensin.

52. The animal feed premix of claim 50 wherein the polyether antibiotic is narasin.

53. The animal feed premix of claim 50 wherein the polyether antibiotic is salinomycin.

54. The animal feed premix of claim 50 wherein the polyether antibiotic is laidlomycin.

55. The animal feed premix of claim 50 wherein the polyether antibiotic is portmicin.

56. The animal feed premix of claim 50 wherein the polyether antibiotic is A82810.

57. An animal feed comprising from 0.0001 to 0.01 percent by weight of a polyether antibiotic and from 0.0001 to 0.01 percent by weight of a carbanilide compound of the formula

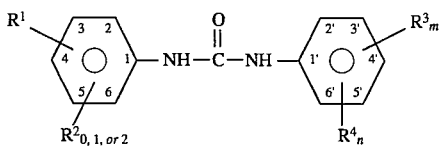

wherein $R^1$ represents perfluoroalkylsulfonyloxy of $C_1$–$C_8$ or 1,1,2,2-tetrafluoroethylsulfonyloxy, with the limitation that if no $R^2$ is present, $R^1$ is located at the 4-position;

$R^3$ represents perfluoroalkylsulfonyloxy of $C_1$–$C_8$ or 1,1,2,2-tetrafluoroethylsulfonyloxy, with the limitation that if no $R^4$ is present, $R^3$ is located at the 4'-position;

each $R^2$ and $R^4$ independently represents nitro, halo, cyano, thiocyanato, trifluoroacetylthio, perfluoroalkyl of $C_1$–$C_2$, 1,1,2,2-tetrafluoroethyl, perfluoroalkoxy of $C_1$–$C_2$, 1,1,2,2-tetrafluoroethoxy, perfluoroalkylthio of $C_1$–$C_2$, 1,1,2,2-tetrafluoroethylthio, perfluoroalkylsulfinyl of $C_1$–$C_2$, 1,1,2,2-tetrafluoroethylsulfinyl, perfluoroalkylsulfonyl of $C_1$–$C_2$, or 1,1,2,2-tetrafluoroethylsulfonyl;

m represents 0 or 1;

n represents 0, 1, or 2; and the sum of m and n is 1, 2, or 3.

58. The animal feed of claim 57 wherein the polyether antibiotic is selected from the group consisting of monensin, narasin, salinomycin, laidlomycin, portmicin, and A82810.

59. The animal feed of claim 58 wherein the carbanilide compound is 4'-(trifluoromethylthio)-4-(trifluoromethylsulfonyloxy)carbanilide.

60. The animal feed of claim 59 wherein the polyether antibiotic is monensin.

61. The animal feed of claim 59 wherein the polyether antibiotic is narasin.

62. The animal feed of claim 59 wherein the polyether antibiotic is salinomycin.

63. The animal feed of claim 59 wherein the polyether antibiotic is laidlomycin.

64. The animal feed of claim 59 wherein the polyether antibiotic is portmicin.

65. The animal feed of claim 59 wherein the polyether antibiotic is A82810.

66. The animal feed of claim 58 wherein the carbanilide compound is 4'-(trifluoromethylsulfonyl)-4-(trifluoromethylsulfonyloxy)carbanilide.

67. The animal feed of claim 66 wherein the polyether antibiotic is monensin.

68. The animal feed of claim 66 wherein the polyether antibiotic is narasin.

69. The animal feed of claim 66 wherein the polyether antibiotic is salinomycin.

70. The animal feed of claim 66 wherein the polyether antibiotic is laidlomycin.

71. The animal feed of claim 66 wherein the polyether antibiotic is portmicin.

72. The animal feed of claim 66 wherein the polyether antibiotic is A82810.

73. The compound of (trifluoromethylsulfonyl)-3-(trifluoromethyl)-4-(perfluoro-n-butylsulfonyloxy)carbanilide.

74. The method of claim 5 wherein the active agent is 4'-(trifluoromethylsulfonyl)-3-(trifluoromethyl)-4-perfluoro-n-butylsulfonyloxy)carbanilide.

75. The method of claim 9 wherein the active agent is 4'-(trifluoromethylsulfonyl)-3-(trifluoromethyl)-4-(perfluoro-n-butylsulfonyloxy)carbanilide.

76. The animal feed premix of claim 13 wherein the active agent is 4'-(trifluoromethylsulfonyl)-3-(trifluoromethyl)-4-(perfluoro-n-butylsulfonyloxy)carbanilide.

77. The animal feed of claim 17 wherein the active agent is 4'-(trifluoromethylsulfonyl)-3-(trifluoromethyl)-4-(perfluoro-n-butylsulfonyloxy)carbanilide.

78. The method of claim 21 wherein the carbanilide compound is 4'-(trifluoromethylsulfonyl)-3-trifluoromethyl)-4 -(perfluoro-n-butylsulfonyloxy)carbanilide.

79. The method of claim 37 wherein the carbanilide compound is 4'-(trifluoromethylsulfonyl)-3-(trifluoromethyl)-4-(perfluoro-n-butylsulfonyloxy)carbanilide.

80. The animal feed premix of claim 41 wherein the carbanilide compound is 4'-(trifluoromethylsulfonyl)-3-(trifluoromethyl)-4-(perfluoro-n-butylsulfonyloxy)carbanilide.

81. The animal feed of claim 57 wherein the carbanilide compound is 4'-(trifluoromethylsulfonyl)-3-(trifluoromethyl)-4-(perfluoro-n-butylsulfonyloxy)carbanilide.

82. The compound of claim 1 which is 4'-(trifluoromethylsulfonyl)-3-(trifluoromethyl)-4 -(trifluoromethylsulfonyloxy)carbanilide.

83. The method of claim 5 wherein the active agent is 4'-(trifluoromethylsulfonyl)-3-(trifluoromethyl)-4-(trifluoromethylsulfonyloxy)carbanilide.

84. The method of claim 9 wherein the active agent is 4'-(trifluoromethylsulfonyl)-3-(trifluoromethyl)-4-(trifluoromethylsulfonyloxy)carbanilide.

85. The animal feed premix of claim 13 wherein the active agent is 4'-(trifluoromethylsulfonyl)-3-(trifluoromethyl)-4-(trifluoromethylsulfonyloxy)carbanilide.

86. The animal feed of claim 17 wherein the active agent is 4'-(trifluoromethylsulfonyl)-3-(trifluoromethyl)-4-(trifluoromethylsulfonyloxy)carbanilide.

87. The method of claim 21 wherein the carbanilide compound is 4'-(trifluoromethylsulfonyl)-3-(trifluoromethyl)-4-(trifluoromethylsulfonyloxy)carbanilide.

88. The method of claim 37 wherein the carbanilide compound is 4'-(trifluoromethylsulfonyl)-3-(trifluoromethyl)-4-(trifluoromethylsulfonyloxy)carbanilide.

89. The animal feed premix of claim 41 wherein the carbanilide compound is 4'-(trifluoromethylsulfonyl)-3-(trifluoromethyl)-4-(trifluoromethylsulfonyloxy)carbanilide.

90. The animal feed of claim 57 wherein the carbanilide compound is 4'-(trifluoromethylsulfonyl)-3-(trifluoromethyl)-4-(trifluoromethylsulfonyloxy)carbanilide.

91. The compound of claim 1 which is 4'-(trifluoromethylsulfonyl)-3-nitro-5-(trifluoromethyl)-4 -(perfluoro-n-butylsulfonyloxy)carbalinide.

92. The method of claim 5 wherein the active agent is 4'-(trifluoromethylsulfonyl)-3-nitro-5-(trifluoromethyl)-4-(perfluoro-n-butylsulfonyloxy)carbanilide.

93. The method of claim 9 wherein the active agent is 4'-(trifluoromethylsulfonyl)-3-nitro-5-(trifluoromethyl)-4-(perfluoro-n-butylsulfonyloxy)carbanilide.

94. The animal feed premix of claim 13 wherein the active agent is 4'-(trifluoromethylsulfonyl)-3-nitro-5-(trifluoromethyl)-4 -(perfluoro-n-butylsulfonyloxy)carbanilide.

95. The animal feed of claim 17 wherein the active agent is 4'-(trifluoromethylsulfonyl)-3-nitro-5-(trifluoromethyl)-4-(perfluoro-n-butylsulfonyloxy)carbanilide.

96. The method of claim 21 wherein the carbanilide compound is 4'-(trifluoromethylsulfonyl)-3-nitro-5-(trifluoromethyl)-4-(perfluoro-n-butylsulfonyloxy)carbanilide.

97. The method of claim 37 wherein the carbanilide compound is 4'-(trifluoromethylsulfonyl)-3-nitro-5-(trifluoromethyl)-4-(perfluoro-n-butylsulfonyloxy)carbanilide.

98. The animal feed premix of claim 41 wherein the carbanilide compound is 4'-(trifluoromethylsulfonyl)-3-nitro-5-(trifluoromethyl)-4 -(perfluoro-n-butylsulfonyloxy)carbanilide.

99. The animal feed of claim 57 wherein the carbanilide compound is 4'-(trifluoromethylsulfonyl)-3-nitro-5-(triftuoromethyl)-4 -(perfluoro-n-butylsulfonyloxy)carbanilide.

100. The compound of claim 1 which is 4'-(trifluoromethylsulfonyl)-3-nitro-5-(trifluoromethyl)-2 -(trifluoromethylsulfonyloxy)carbanilide.

101. The method of claim 5 wherein the active agent is 4'-(trifluoromethylsulfonyl)-3-nitro-5-(trifluoromethyl)-2-(trifluoromethylsulfonyloxy)carbanilide.

102. The method of claim 9 wherein the active agent is 4'-(trifluoromethylsulfonyl)-3-nitro-5-(trifluoromethyl)-2-(trifluoromethylsulfonyloxy)carbanilide.

103. The animal feed premix of claim 13 wherein the active agent is 4'-(trifluoromethylsulfonyl)-3-nitro-5-(trifluoromethyl)-2-(trifluoromethylsulfonyloxy)carbanilide.

104. The animal feed of claim 17 wherein the active agents is 4'-(trifluoromethylsulfonyl)-3-nitro-5-(trifluoromethyl)-2-(trifluoromethylsulfonyloxy)carbanilide.

105. The method of claim 21 wherein the carbanilide compound is 4'-(trifluoromethylsulfonyl)-3-nitro-5-(trifluoromethyl)-2-(trifluoromethylsulfonyloxy)carbanilide.

106. The method of claim 37 wherein the carbanilide compound is 4'-(trifluoromethylsulfonyl)-3-nitro-5-(trifluoromethyl)-2-(trifluoromethylsulfonyloxy)carbanilide.

107. The animal feed premix of claim 41 wherein the carbanilide compound is 4'-(trifluoromethylsulfonyl)-3-nitro-5-(trifluoromethyl)-2 -(trifluoromethylsulfonyloxy) )carbanilide.

108. The animal feed of claim 57 wherein the carbanilide compound is 4'-(trifluoromethylsulfonyl)-3-nitro-5-(trifluoromethyl)-2 -(trifluoromethylsulfonyloxy)carbanilide.

109. The compound of claim 1 which is 4'-(trifluoromethylsulfonyl)-3-nitro-5-(trifluoromethyl)-4 -(trifluoromethyl)-4-(trifluoromethylsulfonyloxy)carbanilide.

110. The method of claim 5 wherein the active agent is 4'-(trifluoromethylsulfonyl)-3-nitro-5-(trifluoromethyl)-4 -(trifluoromethylsulfonyloxy)carbanilide.

111. The method of claim 9 wherein the active agent is 4'-(trifluoromethylsulfonyl)-3-nitro-5-(trifluoromethyl)-4 -(trifluoromethylsulfonyloxy)carbanilide.

112. The animal feed premix of claim 13 wherein the active agent is 4'-(trifluoromethylsulfonyl)-3-nitro-5-(trifluoromethyl)-4-(trifluoromethylsulfonyloxy)carbanilide.

113. The animal feed of claim 17 wherein the active agent is 4'-(trifluoromethylsulfonyl)-3-nitro-5-(trifluoromethyl)-4 -(trifluoromethylsulfonyloxy)carbanilide.

114. The method of claim 21 wherein the carbanilide compound is 4'-(trifluoromethylsulfonyl)-3-nitro-5-(trifluoromethyl)-4-(trifluoromethylsulfonyloxy)carbanilide.

115. The method of claim 37 wherein the carbanilide compound is 4'-(trifluoromethylsulfonyl)-3-nitro-5-(trifluoromethyl)-4-(trifluoromethylsulfonyloxy)carbanilide.

116. The animal feed premix of claim 41 wherein the carbanilide compound is 4'-(trifluoromethylsulfonyl)-3-nitro-5 -(trifluoromethyl)-4-(trifluoromethylsulfonyloxy) carbanilide.

117. The animal feed of claim 57 wherein the carbanilide compound is 4'-(trifluoromethylsulfonyl)-3-nitro-5-(trifluoromethyl)-4-(trifluoromethylsulfonyloxy)carbanilide.

* * * * *